United States Patent
Desbrosses et al.

(10) Patent No.: US 12,357,536 B2
(45) Date of Patent: *Jul. 15, 2025

(54) CONTAINERS WITH SELECTIVE DISSOLVED GAS CONTENT

(71) Applicants: BAXTER INTERNATIONAL INC., Deerfield, IL (US); BAXTER HEALTHCARE SA, Glattpark (CH)

(72) Inventors: Freddy Desbrosses, Thuin (BE); Pierpaolo Padula, Venosa (IT); Caroline Roselyne Dupont, Ixelles (BE); Marin Anh-Thuan Demulier, Jumet (BE); Zouaoui Bourezg, Braine l'Alleud (BE)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 0 days.

This patent is subject to a terminal disclaimer.

(21) Appl. No.: 18/587,014

(22) Filed: Feb. 26, 2024

(65) Prior Publication Data
US 2024/0245581 A1 Jul. 25, 2024

Related U.S. Application Data

(63) Continuation of application No. 17/330,070, filed on May 25, 2021, now Pat. No. 11,944,586.

(51) Int. Cl.
*A61J 1/10* (2006.01)
*A61J 1/20* (2006.01)
(Continued)

(52) U.S. Cl.
CPC .............. *A61J 1/10* (2013.01); *A61J 1/2093* (2013.01); *A61K 33/04* (2013.01); *A61K 45/06* (2013.01); *A61J 1/2048* (2015.05)

(58) Field of Classification Search
CPC ............ A61J 1/2093; A61J 1/10; A61K 33/04; A61K 47/02; A61K 9/0029; A61K 33/00
See application file for complete search history.

(56) References Cited

U.S. PATENT DOCUMENTS

| | | |
|---|---|---|
| 6,572,603 B1 | 6/2003 | Tani et al. |
| 10,478,453 B1 | 11/2019 | Maloney et al. |
| 2007/0026090 A1 | 2/2007 | Tirosh et al. |

(Continued)

FOREIGN PATENT DOCUMENTS

| | | |
|---|---|---|
| CN | 110917209 | 3/2020 |
| EP | 1621178 | 2/2006 |

(Continued)

OTHER PUBLICATIONS

Allwood et al. Compatibility and Stability of Additives in Parenteral Nutrition Admixtures. Nutrition 1998, vol. 14, No. 9, pp. 697-706.

(Continued)

*Primary Examiner* — Guy K Townsend
*Assistant Examiner* — Seth Han
(74) *Attorney, Agent, or Firm* — K&L Gates LLP

(57) ABSTRACT

The invention relates to a flexible container/multi-chamber container with selective dissolved gas content for stabilizing at least one compound of a medical product having a selective gas requirement for remaining stable, comprising a solution comprising the at least one compound and a fil material from which the container is made that provides for high gas-barrier for the said gas. The at least one compound may be selenium in the form of Se(IV) and is preferably selected from the group consisting of sodium selenite, selenous acid and selenium dioxide. The selective gas may be oxygen, and the headspace of the oxygen maintains the solution to comprise dissolved oxygen (DO) at a level of 0.5 ppm to 8 ppm.

39 Claims, 14 Drawing Sheets

(51) Int. Cl.
*A61K 33/04* (2006.01)
*A61K 45/06* (2006.01)

(56) References Cited

U.S. PATENT DOCUMENTS

| | | | |
|---|---|---|---|
| 2009/0076014 A1* | 3/2009 | Oppenheimer | A61K 45/06 |
| | | | 514/249 |
| 2009/0317611 A1 | 12/2009 | Mueller et al. | |
| 2012/0288572 A1 | 11/2012 | Kugelmann et al. | |
| 2015/0320712 A1 | 11/2015 | Horiuchi et al. | |
| 2019/0046561 A1* | 2/2019 | Perricone | C02F 1/30 |
| 2022/0117843 A1* | 4/2022 | Caronzolo | A61K 9/0019 |

FOREIGN PATENT DOCUMENTS

| | | |
|---|---|---|
| EP | 2080501 | 7/2009 |
| KR | 10-20190105737 | 9/2019 |
| WO | 00/10576 | 3/2000 |
| WO | 2008/050837 | 5/2008 |
| WO | WO-2008050837 A1 * | 5/2008 ............... A61J 1/00 |
| WO | 2009021094 | 2/2009 |
| WO | 2022/251106 | 12/2011 |
| WO | 2019/232054 | 12/2019 |
| WO | 2020/210509 | 10/2020 |

OTHER PUBLICATIONS

Transmittal of International Preliminary Report on Patentability for App. No. PCT/US2022/072505 dated Aug. 1, 2023 (25 pages).
Written Opinion for App. No. PCT/US2022/072505 dated May 4, 2023 (9 pages).
Transmittal of International Search Report and Written Opinion for App. No. PCT/US2022/072505 dated Aug. 31, 2022 (58 pages).

* cited by examiner

CONTAINERS WITH SELECTIVE DISSOLVED GAS CONTENT

CROSS-REFERENCE TO RELATED APPLICATIONS

The present application is a continuation of U.S. patent application Ser. No. 17/330,070, filed on May 25, 2021, the disclosure of which is incorporated herein by reference for all purposes.

DESCRIPTION

The invention generally relates to the field of IV solutions, specifically to the field of clinical nutrition, and corresponding medical products.

The invention relates to a medical product preferably having multiple chambers, with each of the chambers having selective and controllable dissolved gas (e.g., oxygen) content.

In certain embodiments, the invention relates to a flexible container or multi-chamber container with selective dissolved gas content in one or more compartments for stabilizing at least one compound being sensitive to the level of a gas. In certain embodiments, such compounds can be compounds that are provided intravenously, such as, for example, certain vitamins or micronutrients (e.g., selenium compounds in the form of Se(IV)). In certain embodiments, the invention relates to a flexible container or multi-chamber container with selective dissolved gas content in one or more compartments, wherein the headspace of the compartment having certain gas requirements is filled with the required gas (e.g., an ambient air, oxygen-enriched air or oxygen). In case of selenium, the selenium compound in the form of Se(IV) is preferably selected from the group consisting of sodium selenite, selenous acid and selenium dioxide, and the headspace of the compartment containing the solution comprising selenium comprises oxygen as part of ambient air, oxygen enriched ambient air or oxygen, thereby maintain the level of, for example, dissolved oxygen (DO) in the solution at the intended level, such as, for example, 0.5 ppm to 8 ppm of oxygen. Other compounds having specific gas requirements can be envisioned.

In certain embodiments of the invention, the solution of the medical product of the invention comprises at least one additional trace element, such as for example, selenium. As used herein, the expression "medical product" encompasses IV solutions and parenteral and nutrition solutions. The expression "parenteral nutrition solution" refers to a solution for providing nutritional support which is given completely via the bloodstream, intravenously with an IV pump. It contains amino acids, carbohydrates, lipids, electrolytes, vitamins, and/or minerals. The medical solution may be ready-to-use. The solution may be contained in one chamber of a multi-chamber container having at least two, at least three, at least four, at least five, at least six or more chambers. It can also be contained in a mono-bag. More than one solution contained in a multi chamber bag may have specific gas requirements, such as elevated oxygen levels, which may be different from the remaining compartments of the multi chamber bags, that, for example, may require especially low levels of oxygen. Furthermore, the invention relates to a method of providing a medical product in a multi-chamber container according to the invention or, potentially, in a monobag according to the invention.

BACKGROUND OF THE INVENTION

Solutions for intravenous administration, including parenteral nutrition (PN) products aim to supply certain compounds to patients by venous access. For example, parenteral nutrition products can be composed of macronutrients (lipids, amino acid or protein and dextrose or carbohydrates), micronutrients (vitamins and trace elements) and/or electrolytes. IV solutions and PN products are often provided in flexible bags having different volumes. Especially PN products are often provided in multi-chamber bags because different formulations, such as the mentioned lipid formulations, carbohydrate formulations or amino acid formulations must be kept apart from each other during production, filling, sterilization, and storage so they remain stable. The various formulations often have different requirements as to, for example, pH, the presence of certain active ingredients or excipients that may impact stability or interact with each other, and the presence or absence of certain gases, such as, for example, oxygen, which tends to react with many pharmaceutically active ingredients and renders them inactive.

Still, while different formulations may be located in different compartments of, for example, a multi-chamber bag as typically used in parenteral nutrition, different requirements as to a specific gas that must or must not be present in different formulation of the same MCB are difficult to realize. As will be readily understood, a multi-chamber bag is prepared from one film material. Different compartments are introduced by welding seals between the different compartments which may be (partially) permanent or peelable, e.g. under manual pressure. Accordingly, if one or more of the formulations require the use of a certain film material, e.g. an oxygen semipermeable film material that allows oxygen to slowly be removed from a given formulation by means of an oxygen absorber placed, for example, in the overpouch to keep oxygen levels low in said formulations, it is difficult to also accommodate a compartment and formulation that requires, for example, high oxygen levels and, in consequence, a high oxygen barrier film material to avoid oxygen leaving the compartment, especially if there is also an oxygen absorber present in the overpouch.

Further challenges occur if the compound having selective gas requirements for its stability, such as a compound requiring high dissolved oxygen levels. Oxygen may be consumed by a component of the formulation and/or may be lost even in case of using a high oxygen barrier material by diffusion through the film. This is especially pronounced in the presence of an oxygen absorber which may be located in the overpouch of a MCB and will slowly deplete the solution of dissolved oxygen, also in case of a high oxygen barrier material. Once oxygen has been lost from the compartment, the compound will start to lose stability and will be degraded. So, just using a film material for a container which has a high oxygen barrier to reduce the loss of DO from the solution through the container may not be enough to address the problem of such compounds over a prolonged time, i.e. typical shelf-life requirements for ready-to-use pharmaceutical formulations that generally should be at least 6, 12, 18 or best 24 months at temperatures of up to 25° C.

Also parenteral nutrition solutions, such as in the form of one or more solutions, can be provided in the form of flexible bags, either in the form of single flexible bags containing glucose, amino acids or lipids with or without electrolytes, or any other solutions that may contain, for example, vitamins and/or trace elements, and which can be mixed together prior administration, or in the form of multi-chamber flexible bags as mentioned above providing separated macronutrients and electrolytes, in a ready to use format. The same issue of incompatible gas level requirements in different formulations may therefore also occur in MCBs providing parenteral nutrition formulations.

It is known that such headspace is created when liquid compositions are introduced into containers, such as the containers discussed herein, meaning that air is trapped at the top of the container before it can be sealed. Generally, it is the goal in the industry to reduce headspace for various reasons. Methods have been developed to monitor headspace oxygen levels in pre-filled containers arising requirement to ensure the stability and potency of oxygen-sensitive product, such as, for example, headspace oxygen analysis (HOA), or non-destructive laser-based headspace inspection, which is a method used for the inspection of finished sterile products. As described also in WO2009021094A1, headspace can be reduced by various methods, including the "topping off" of the container with a sufficient amount of the composition to prevent air from remaining at the top of the container or the venting of liquid-filled containers. Another technique is to provide elaborate passages in a closure whereby gases may leave the system, but liquid losses are minimized. Another system makes use of one or more tiny orifices in rubber, metal or plastic diaphragms which render the material permeable to gases. If it cannot be completely avoided to have a headspace, which is generally the case, it is filled with an inert gas such as nitrogen.

In summary, headspace in the prior art in, for example, containers for pharmaceutical solutions, is either sought to be reduced and avoided, where possible, or controlled in a way to avoid the presence of any non-inert gases, such as oxygen.

Typical medical solution containers, including those used for parenteral nutrition solution, must meet a number of performance criteria, including flexibility, transparency, gas barrier property, drug compatibility, heat sterilization resistance, fall impact resistance, etc. Various types of medical solution containers are now available, for example, a double bag with an inner bag and outer bag, where the inner bag contains functional medical solutions and the outer bag (also referred to as "overpouch") covers the inner bag and has gas or oxygen blockage function.

The bags are typically made of a synthetic or plastic material, for example materials such as polypropylene (PP), polyethylene (PE), ethylene vinyl alcohol (EVOH), ethylene-vinyl acetate (EVA) and all possible copolymers, essentially any synthetic material suitable for containing the components to be administered.

As mentioned above, in the state of the art, micronutrients but also certain drugs are typically added to nutrition bags directly before administration because they cannot be stably formulated into one of the MCB's compartments. For this purpose, vitamins can be provided in glass vials in the form of lyophilizates or solutions to be reconstituted and/or mixed into the nutrition/infusion bags. Trace elements are also provided in glass vials or polypropylene ampules meant to be mixed into infusion bags prior to administration. The same is true for certain drugs that could or would typically be added to a parenteral nutrition solution for administration.

Prior to usage, referring to the start of administering the formulation to the patient, the micronutrients or drugs are sometimes added to the mixture or macronutrients via an injection port of the container or bag (septum) or are added via a Y-connector to the infusion line. This process takes time and several handling steps increasing the risk of errors or contamination.

To avoid these potential problems, products have been developed that already contain, for example, some trace elements in nutrition multi-chamber bags. For example, Pediaven, a parenteral nutrition binary solution intended for infants, children and adolescents, contains trace elements in the glucose chamber. However, it has been reported that the trace element selenium, provided as selenium dioxide in the product, is absent in the finished product potentially due to degradation, as announced in July 2014 (http://www.pharmacovigilance-tours.fr/490.html). Another product, Elneopa, from Otsuka Pharmaceuticals, contains certain trace elements in a small dedicated chamber as part of a multi-chamber bag. However, this product does not contain selenium.

For example, EP2080501A1 discloses a multi-chamber bag comprising formulations for parenteral nutrition, including also micronutrients (trace elements) which seeks to reduce the dissolved oxygen content in the formulations by using a plastic material having an oxygen permeability of not lower than 200 $cm^3/m^2$. 24 h·atm at a temperature of 25° C. at a humidity of 60% RH within 12 hours after a steam sterilization process or a hot water sterilization process and having a steady-state oxygen permeability of not higher than 100 $cm^3/m^2$. 24 h·atm at a temperature of 25° C. at a humidity of 60% RH. In such case, the dissolved oxygen levels are bound to be significantly reduced over time, especially over shelf-life, which is beneficial for oxygen-prone components, but would lead to the degradation of Se(IV) if present as a micronutrient.

KR10-2019-0105737 relates to an infusion solution preparation containing fat-soluble vitamins and trace elements, and more particularly, to an infusion solution preparation which includes a plurality of chambers therein and thus stores reducing sugars, amino acids, lipids and fat-soluble vitamins, and trace elements separately. The publication, among other trace elements contained in a chamber of a multi-chamber nutritional product, also mentions selenium ions and a preferred concentration of 3 µg/mL to 7.0 µg/ml based on a selenium cation. Specific ions or ways to stabilize such selenium ions in the formulation are not mentioned.

It is known in the art that, for example, selenium, iodine and copper—especially in combination—are difficult to include in nutrition bags, as they can undergo chemical reactions, especially as they have to undergo extreme conditions such as a heat sterilization and extended storage periods (for example, Allwood et al. Compatibility and Stability of Additives in Parenteral Nutrition Admixtures. Nutrition 1998, Vol. 14, No. 9, pp. 697-706; Eisenberg et al. Stability of selenium sources reviewed. Feedstuffs, Jun. 18, 2012).

Furthermore, in various formulation studies, when attempting to introduce trace elements into nutrition multi-chamber bags, serious stability issues have been experienced, in particular the loss of selenium has been observed. This may be due to the fact that selenium in the form of Se(IV) and specifically in the form of sodium selenite, selenious acid or selenium dioxide is prone to adsorption, for example to plastic materials or iron oxides; can be reduced into metallic selenium in the presence of reducing agents like ascorbic acid; can be reduced into hydrogen selenide, which is a volatile substance; and/or can be transformed into selenious dioxide at low pH, which is also a volatile substance under certain conditions. In short, the conditions for certain compounds such as selenite are not appropriate in a MCB to provide it in a stable manner. Such issue can now be addressed as disclosed herein. As a consequence of the disclosure made herein, it will now be possible to stably provide ready-to-use medical products or flexible container/ multi-chamber containers for medical products, including those for parenteral administration, that comprise a solution for parenteral administration to a patient in need thereof, comprising a compound with a selective gas requirement that may even contrast with the requirements of other formulations in the same MCB. For example, selenium in the form of Se(IV) can now be provided stably over a prolonged period of time. The technology as disclosed herein can also be used for other compounds or combination of compounds which have a selective gas requirement, specifically in the context of multi-chamber bags that comprise formulations having conflicting requirements in terms of various gas levels in the solutions.

There is, therefore, a remaining need to provide for solutions that allow the accommodation of sensitive compounds that require a selective gas to be present in a formulation, especially in a formulation being part of a MCB that encompasses further formulations having different gas level requirements.

SUMMARY OF THE INVENTION

In one aspect, the present invention relates to a flexible container with selective dissolved gas content for stabilizing at least one compound of a medical product having a selective gas requirement for remaining stable, the flexible container comprising: a solution comprising the at least one compound; a film material from which the container is made that provides for a high gas-barrier with regard to the said gas; and a headspace of the gas.

According to another aspect, the present invention relates to a flexible container with selective dissolved gas content for stabilizing at least one compound of a medical product, the flexible container comprising:
 (a) a solution comprising the at least one compound having a selective dissolved gas requirement; and
 (b) a headspace of the gas.

According to another aspect, the at least one compound is a compound requiring high levels of oxygen, and the selective dissolved gas is oxygen.

According to another aspect, the flexible container is a multi-chamber bag comprising at least one chamber wherein the compound having a selective dissolved gas requirement is located.

According to another aspect, the flexible container has a volume of the headspace from about 5% to about 100% of the volume of the solution in the flexible container.

According to another aspect, the volume of the headspace is about 35% to 45% of the volume of the solution in the flexible container.

According to another aspect, the container is terminally heat-sterilized.

According to another aspect, the at least one compound is a selenium compound in the form of Se(IV).

According to another aspect, the at least one selenium compound is selected from the group consisting of sodium selenite, selenous acid and selenium dioxide.

According to another aspect, the solution comprises equal or above 0.5 ppm dissolved oxygen (DO) throughout shelf life of the medical product.

According to another aspect, the solution comprises from about 0.5 ppm to about 8 ppm dissolved oxygen (DO).

According to another aspect, the solution comprises equal or above 1 ppm dissolved oxygen (DO).

According to another aspect, the concentration of dissolved oxygen (DO) in the solution at the time of sterilization is at least 6 ppm.

According to another aspect, the headspace of the gas stabilizes the at least one compound for a time selected from the group consisting of at least 3 months, at least 6 months, at least 12 months, at least 18 months, and at least 24 months when stored at a temperature between about 1° C. and about 40° C.

According to another aspect, the flexible container is stored at a temperature between about 18° C. and about 30° C.

According to another aspect, the solution has an acidic pH value in the range of from about 1 to about 4, preferably from about 2.5 to about 3.2.

According to another aspect, the multi-chamber container comprises at least two chambers.

According to another aspect, the multi-chamber container is selected from the group consisting of a two-chamber container, a three-chamber container, a four-chamber container, a five-chamber container, a six-chamber container, a seven-chamber container, and an eight-chamber container.

According to another aspect, the multi-chamber container comprises:
 (a) a first chamber containing a carbohydrate formulation;
 (b) a second chamber containing an amino acid formulation;
 (c) a third chamber containing a lipid formulation; and
 (d) a fourth chamber containing a solution comprising a compound having a selective dissolved gas requirement.

According to another aspect, the solution contained in the fourth chamber comprises at least one selenium compound and wherein the headspace is filled with ambient air, oxygen enriched ambient air, or oxygen.

According to another aspect, the flexible container is made of a material having an oxygen barrier of less than 1 cc/m$^2$/day, preferably of less than 0.5 cc/m$^2$/day.

According to another aspect, the compartment of the flexible container wherein the compound having a selective dissolved gas requirement is located comprises a gas-tight port tube or no port tube.

According to another aspect, the invention relates to a multi-chamber container with selective dissolved gas content for stabilizing at least one micronutrient of a medical product, the multi-chamber container comprising:
 (a) a first chamber comprising a carbohydrate formulation, an amino acid formulation or a lipid formulation;
 (b) a second chamber comprising a solution comprising the at least one micronutrient having a selective dissolved gas requirement; and a headspace of the gas.

According to another aspect, the at least one micronutrient is at least one micronutrient compound is selenium in the form of Se(IV), and the dissolved gas is dissolved oxygen (DO).

According to another aspect, the multi-chamber container comprises at least five chambers.

According to another aspect, the at least one selenium compound is selected from the group consisting of sodium selenite, selenous acid and selenium dioxide.

According to another aspect, the at least one selenium compound is sodium selenite or selenium dioxide.

According to another aspect, the solution of the second chamber comprises equal or above 0.5 ppm dissolved oxygen (DO) throughout shelf life of the medical product.

According to another aspect, the solution of the second chamber comprises from about 0.5 ppm to about 8 ppm dissolved oxygen (DO).

According to another aspect, the solution of the second chamber comprises equal or above 1 ppm dissolved oxygen (DO).

According to another aspect, the container is terminally heat-sterilized.

According to another aspect, the concentration of dissolved oxygen (DO) in the solution at the time of sterilization is at least 6 ppm.

According to another aspect, the volume of the headspace is from about 5% to about 100% of the volume of the solution in the multi-chamber container.

According to another aspect, the volume of the headspace of the oxygen is about 35 to about 45% of the volume of the solution in the flexible container.

According to another aspect, the headspace of the gas stabilizes the at least one micronutrient for a time selected from the group consisting of at least 3 months, at least 6 months, at least 12 months, at least 18 months, and at least 24 months when stored at a temperature between about 1° C. and about 30° C.

According to another aspect, the multi-chamber container is stored at a temperature between about 18° C. and about 25° C.

According to another aspect, the multi-chamber container is made of a material having an oxygen barrier less than 1 cc/m²/day, preferably less than 0.5 cc/m²/day.

BRIEF DESCRIPTION OF THE DRAWINGS

The invention is further described by the following figures. These are not intended to limit the scope of the invention but represent preferred embodiments of aspects of the invention provided for greater illustration of the invention described herein.

FIG. 13 shows about 80% fit between Se dosage and log oxygen content.

DETAILED DESCRIPTION OF THE INVENTION

Figure 1:
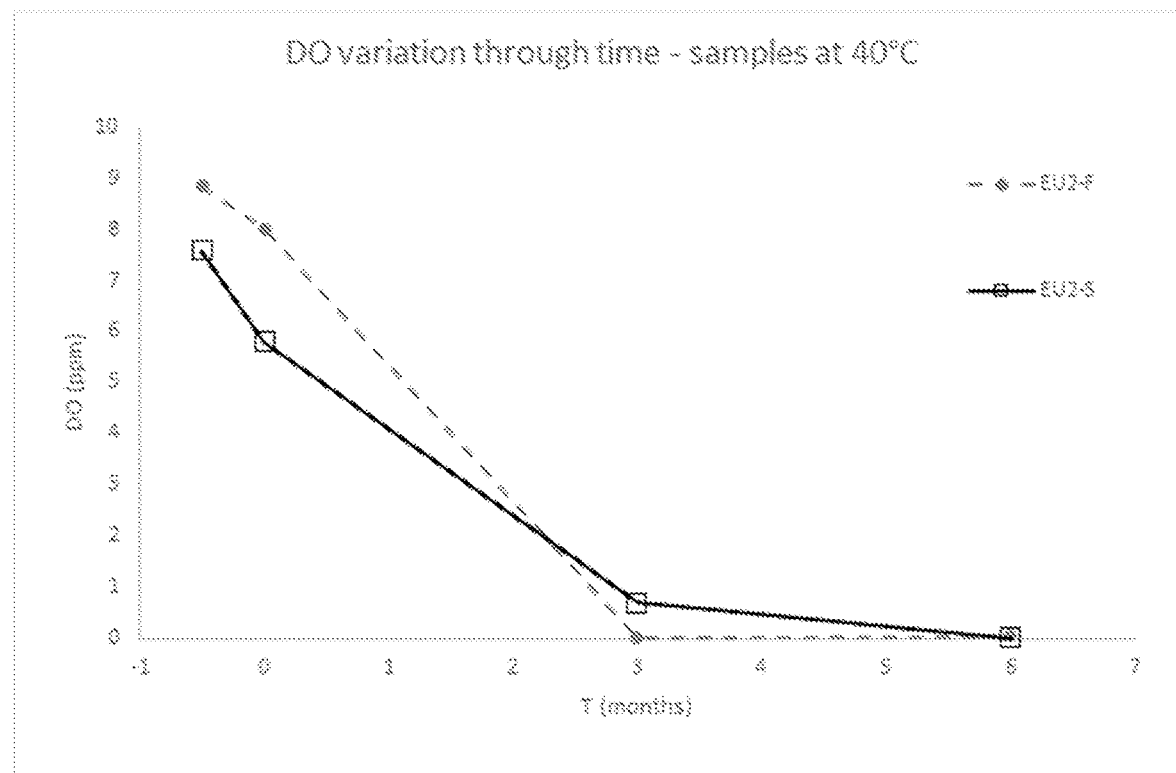
FIG. 1 is a set of graphs showing dissolved oxygen (DO) variation through time at 40° C. for samples of the EU-2S batch (semi-permeable) and the EU2-F bag (oxygen-impermeable).

Unless defined otherwise, all technical and scientific terms used herein have the same meaning as commonly understood by one of ordinary skill in the art to which this invention belongs. As used herein the following terms have the following meanings.

The term "comprising" or "comprises," as used herein, is intended to mean that the compositions and methods include the recited elements, but not excluding others.

The term "about," when used before a numerical designation, e.g., temperature, time, amount, and concentration, including range, indicates approximations which may vary by (+) or (−) 10%, 5% or 1%.

In the context of the invention the terms "flexible bag" and "flexible container" may be used interchangeably. The terms "solution" and "formulation" are also used interchangeably in the context of the present invention.

The term "micronutrient," as used herein, refers to any essential element required by organisms in varying quantities throughout life to orchestrate a range of physiological functions to maintain health. Important micronutrients include iodine, iron, zinc, calcium, selenium, fluorine, and vitamins A, $B_6$, $B_{12}$, $B_1$, $B_2$, $B_3$, $B_9$, K and C. For human nutrition, micronutrient requirements may be in amounts generally less than 100 milligrams per day, whereas macronutrients may be required in gram quantities daily. Calcium is also referred to as an electrolyte, as the case may be.

The term "macronutrient," as used herein, refers to a class of chemical compounds which humans consume in relatively large quantities compared to vitamins and minerals, and which provide humans with energy. There are three principal classes of macronutrients: carbohydrate, protein, and fat.

As disclosed herein, the term "medical product" relates to any product intended to be used for medical purposes, preferably for clinical nutrition. The medical product of the invention is intended and designed for the medical purpose of preventing or correcting selenium deficiency in a patient.

As disclosed herein, the term "dissolved oxygen" (DO) refers to the level of free, non-compound oxygen present in water or other liquids or solutions, such as solutions for parenteral nutrition. Oxygen saturation (symbol $SO_2$) is a relative measure of the concentration of oxygen that is dissolved or carried in a given medium as a proportion of the maximal concentration that can be dissolved in that medium. It can be measured with a dissolved oxygen probe such as an oxygen sensor or an optode in liquid media, usually water.

Dissolved oxygen is usually reported in milligrams per liter (mg/L) or as a percent of air saturation. However, studies also report DO in parts per million (ppm) or in micromoles (μmol). 1 mg/L is equal to 1 ppm. The relationship between mg/L and % air saturation varies with temperature, pressure and salinity of the water. One micromole of oxygen is equal to 0.022391 milligrams. Thus 100 µmol/L $O_2$ is equal to 2.2 mg/L $O_2$. To calculate dissolved oxygen concentrations from air saturation, it is necessary to know the temperature and salinity of the sample. Barometric pressure has already been accounted for as the partial pressure of oxygen contributes to the percent air saturation. Salinity and temperature can then be used in Henry's Law to calculate what the DO concentration would be at 100% air saturation. However, it is easier to use an oxygen solubility chart. These charts show the dissolved oxygen concentration at 100% air saturation at varying temperatures, and salinities. This value can then be multiplied by the measured percent air saturation to calculate the dissolved oxygen concentration [Fondriest Environmental, Inc. "Dissolved Oxygen." Fundamentals of Environmental Measurements. 19 Nov. 2013.].

Oxygenation of liquids occurs for example through exposure of the liquids to gases containing oxygen. For example, exposure of a liquid sample to the atmosphere comprising around 21% $O_2$ leads to oxygenation through diffusion of the gaseous oxygen into the liquid. This process can be accelerated for example by stirring, flushing the liquid with an oxygen-containing gas or similar techniques known to the skilled person.

There are several methods available in the art for measuring dissolved oxygen concentrations. Modern techniques involve either an electrochemical or optical sensor, where the dissolved oxygen sensor is attached to a meter for spot sampling and laboratory applications or to a data logger, process monitor or transmitter for deployed measurements and process control. An example is the fiber-optic oxygen meter Microx TX3 from PreSens Precision Sensing GmbH (Germany) for gaseous and dissolved $O_2$. The colorimetric method offers a basic approximation of dissolved oxygen concentrations in a sample. There are two methods designed for high-range and low-range dissolved oxygen concentrations. These methods are quick and inexpensive for basic projects but limited in scope and subject to error due to other redoxing agents that may be present in the water. The traditional method is the Winkler titration.

As used herein, the term "shelf life" relates to the length of time that the medical product within the flexible container/multi-chamber container of the present invention can be stored without becoming unfit for use or consumption at defined storage conditions after sealing and sterilizing. Depending on the storage conditions, a shelf life may vary.

As used herein, the term "stable", "stably" or "stability" means that at least 50%, at least 60%, at least 70% or at least 80% of the amount of a component, specifically a compound having a selective gas requirement, provided in the product at the time it is produced is still available, preferably also after terminal heat-sterilization, for at least 6 months, preferably for at least 12 months, and more preferably for at least 18 months and even more preferably for at least 24 months at a temperature of from 1° C. to 40° C., such as at temperatures of from 1° C. to 30° C. Preferably, at least 80%, at least 85%, at least 90% and at least 95% of the component at the time it is produced is still available, preferably also after terminal heat-sterilization, for at least 6 months, preferably for at least 12 months, at a temperature of from 1° C. to 40° C. and/or for at least 18 months and preferably for at least 24 months at a temperature of from 1° C. to 30° C. The expression "at the time it is produced" refers to the time immediately before terminal heat-sterilization.

In light of the prior art the technical problem underlying the present invention is to provide a flexible container/multi-chamber container comprising at least one solution having a selective dissolved gas content for stabilizing at least one compound having such selective gas requirement (e.g., the aforementioned selenium compound in the form of Se(IV)). Specifically, the problem relates to providing a multi-chamber bag which comprises at last two formulations having different dissolved gas requirements, such as for example, the one having the requirement of maintaining a very low level of a gas over a prolonged time, and the other one having the requirement of maintaining a high or higher level of the same gas over a prolonged time for the respective stability of the formulation or the compounds comprised therein. As mentioned before, a MCB is generally prepared from one film material which cannot individually be adapted to the said diverging gas requirements. So, in certain cases, a film material will be selected that allows gas to diffuse out of the formulation to be captured by a scavenger located outside of the primary container, such as, for example, an oxygen scavenger that will consume oxygen that is still present to some extent in a formulation where oxygen is not wanted. However, this is opposed by the need to retain the potentially same gas in a second compartment, such as oxygen that must remain over a certain concentration threshold to guarantee that at least one compound contained in said compartment remains stable.

This issue of different, selective gas requirements of formulations to be accommodated in one multi-chamber bag was not addressed and solved so far in the prior art. Accordingly, compounds requiring a selective dissolved gas content in the formulation that is opposed to the requirements of another formulation are not provided in one MCB, but are generally added to the MCB, generally after reconstitution and before administration to the patient, or are provided in a second medical solution.

This problem is solved by the features of the independent claims. Preferred embodiments of the present invention are provided by the dependent claims.

It was found that there is a relatively simple but highly efficient way to stabilize compounds having certain selective gas requirements in a container as described above. The method can be used for mono-bags made from rigid, semi-rigid or flexible containers, and is especially suitable for multi-chamber containers wherein formulations are stored that have very different requirements regarding such selective gas.

The invention therefore relates to a flexible container/multi-chamber container with selective dissolved gas (content for stabilizing at least one compound of a medical product, comprised in the or one of the compartment(s) of the container/multi-chamber container, wherein the container is prepared from a gas barrier film material regarding the selective dissolved gas in question, and a headspace that comprises the said gas, wherein the headspace of the gas serves as a reservoir of the gas that is required by the at least one compound to be stabilized in the container.

The expression "headspace" as it is used herein refers to the unfilled space in a container holding a liquid or a solid.

Headspace in the prior art in, for example, headspace in containers for medical solutions, is either sought to be reduced and avoided, where possible, or controlled in a way to avoid the presence of any non-inert gases, such as oxygen.

It is, therefore, a very different and non-obvious approach to stabilize compounds requiring certain dissolved gas levels for stability by providing them in a solution comprised in a container or compartment of a container with a deliberately created headspace which is filled with a reservoir gas that can replenish said dissolved gas that, for example, gets lost through the film material, specifically in cases where gas scavengers such as, for example, oxygen absorbers are used to satisfy the needs of other formulations which may be located in the same MCB.

The headspace filled with the required gas or mixtures of gases can advantageously combined with a film material that has a high barrier to the gas in question. According to one embodiment, the flexible container/multi-chamber container is made of an oxygen-impermeable material having an oxygen or carbon dioxide barrier less than 5 cc/m$^2$/day, less than 2 cc/m$^2$/day, less than 1 cc/m$^2$/day, and preferably less than 0.5 cc/m$^2$/day, such as for example, less than 0.2 cc/m$^2$/day, less than 0.3 cc/m$^2$/day or less than 0.4 cc/m$^2$/day. In case the film material has a somewhat lower oxygen or carbon dioxide barrier, the corresponding headspace and/or the concentration of the selective gas can be increased to stock more of the selective gas to keep the dissolved gas levels above the desired threshold over a prolonged time. Using a film material with a higher oxygen barrier may allow to reduce the headspace and/or the concentration of the selective gas in the headspace.

Specifically, it was found that it is possible to accommodate one or more formulations having selective gas requirements in a container, such as, for example, a multi-chamber container having at least two compartments, by the deliberate use of headspace serving as a reservoir for the required gas or gas mixture that can replenish the used up dissolved gas in the solution comprising the compound requiring a gas for stability, while at the same time a film is used for producing the container that has a low permeability for the said gas, especially if the container contains further compartments and formulations that require low or at least lower levels of the same gas and therefore often comprise a gas scavenger in the packaging, for example in the overpouch which is wrapped around the primary container containing said various formulations.

As will be readily understood, some gas will permeate through the container film used over a prolonged time, even if the material creates a high gas barrier. This is even more pronounced when the container has an overpouch which comprises a gas scavenger which draws on the dissolved gas. This may also be desirable, to a certain extent, if other formulations in a MCB require that gas, such, for example, oxygen, including oxygen produced within the formulations over time, must be removed from the solution by allowing the oxygen to pass the barrier and be absorbed by such scavenger.

According to one embodiment, the selective dissolved gas is oxygen, which is usually avoided as a dissolved gas in medical solutions as it may lead to the oxidation and degradation of the included active ingredients. However, the invention can equally well be applied to other selective gases that are required for maintaining the stability of a compound provided in a medical solution. The invention expressly does not refer to and/or encompass dissolved gases such as nitrogen or other inert gases which are used to replace any non-inert gases. Accordingly, the present invention expressly disclaims nitrogen. In a preferred embodiment, the selective dissolved gas is oxygen.

The skilled person will be aware that the concentration of dissolved oxygen (DO) in water is influenced by a number of factors, including water temperature, salinity and atmospheric pressure. Table I provides for the solubility of oxygen in ppm as a function of temperature (760 mmHg, salinity=0.0 ppt). Accordingly, a DO concentration of about 8 ppm corresponds to a solution which is saturated with oxygen at about room temperature (approx.) 21° C.

According to one embodiment of the invention, the DO in the medical solution is above 6 ppm and preferably is from 6 ppm to about 8 ppm at the time of filling and before sterilization, wherein the solution has a temperature of from about 18° C. to about 25° C., preferably of about 21° C.

TABLE I

Solubility of oxygen in ppm (corresponding to mg/L) as a function of temperature from 0° C. to 25° C. (760 mm Hg, salinity = 0.0 ppt)

| T (C. °) | 0.0 | 0.2 | 0.4 | 0.6 | 0.8 |
|---|---|---|---|---|---|
| 0 | 14.602 | 14.520 | 14.438 | 14.358 | 14.278 |
| 1 | 14.198 | 14.120 | 14.042 | 13.969 | 13.889 |
| 2 | 13.813 | 13.738 | 13.664 | 13.591 | 13.518 |
| 3 | 13.445 | 13.374 | 13.303 | 13.233 | 13.163 |
| 4 | 13.094 | 13.025 | 12.957 | 12.890 | 12.823 |
| 5 | 12.757 | 12.692 | 12.627 | 12.563 | 12.499 |
| 6 | 12.436 | 12.373 | 12.311 | 12.249 | 12.188 |
| 7 | 12.127 | 12.067 | 12.008 | 11.949 | 11.980 |
| 8 | 11.832 | 11.774 | 11.717 | 11.661 | 11.604 |
| 9 | 11.549 | 11.493 | 11.439 | 11.384 | 11.331 |
| 10 | 11.277 | 11.224 | 11.172 | 11.119 | 11.068 |
| 11 | 11.016 | 10.995 | 10.915 | 10.865 | 10.815 |
| 12 | 10 766 | 10.717 | 10.669 | 10.620 | 10.573 |
| 13 | 10.525 | 10.478 | 10.432 | 10.386 | 10.340 |
| 14 | 10.294 | 10.249 | 10.204 | 10.160 | 10.115 |
| 15 | 10.072 | 10.028 | 9.985 | 9.942 | 9.900 |
| 16 | 9.858 | 9.816 | 9.774 | 9.733 | 9.692 |
| 17 | 9.651 | 9.611 | 9.571 | 9.531 | 9.492 |
| 18 | 9.453 | 9.414 | 9.375 | 9.337 | 9.299 |
| 19 | 9.261 | 9.224 | 9.187 | 9.150 | 9.113 |
| 20 | 9.077 | 9.040 | 9.004 | 8.969 | 8.933 |
| 21 | 8.989 | 8.863 | 8.829 | 8.794 | 8.760 |
| 22 | 8.726 | 8.693 | 8.659 | 8.626 | 8.583 |
| 23 | 8.560 | 8.528 | 8.495 | 8.463 | 8.431 |
| 24 | 8.400 | 8.368 | 8.337 | 8.306 | 8.275 |
| 25 | 8.244 | 9.214 | 8.184 | 8.153 | 8.124 |
| 26 | 8.094 | 8.065 | 8.035 | 8.006 | 7.977 |
| 27 | 7.949 | 7.920 | 7.892 | 7.864 | 7.836 |
| 28 | 7.808 | 7.780 | 7.753 | 7.725 | 7.698 |
| 29 | 7.671 | 7.645 | 7.618 | 7.592 | 7.565 |

According to one specific embodiment, the compound to be stabilized according to the invention is selenium in its Se(IV) form. Specifically, selenium in its Se(IV) form may be provided in medical solutions for parenteral nutrition. It is known in the art that, for example, selenium, iodine and copper are difficult to include in nutrition bags, as they can undergo chemical reactions, especially under extreme conditions such as a heat sterilization step and during the storage period. See, for example, Allwood et al. Compatibility and Stability of Additives in Parenteral Nutrition Admixtures. Nutrition 1998, Vol. 14, No. 9, pp. 697-706; Eisenberg et al. Stability of selenium sources reviewed. Feedstuffs, Jun. 18, 2012. Therefore, in one embodiment, the at least one compound is selenium in the form of Se(IV) and is preferably selected from the group consisting of sodium selenite, selenous acid and selenium dioxide, and the headspace of the oxygen maintains the solution to comprise dissolved oxygen (DO) at a level of 0.5 ppm to 8 ppm.

In one embodiment, the present invention also relates to a medical product within the flexible container/multi-chamber container for preventing or correcting selenium deficiency in a patient comprising a solution provided in an oxygen-impermeable flexible container for parenteral administration and comprising at least one selenium compound in the form of Se(IV), which is preferably selected from the group consisting of sodium selenite, selenous acid and selenium dioxide, characterized in that the solution comprises dissolved oxygen (DO), preferably 0.5 ppm to 8 ppm DO.

It may be preferable, in certain embodiments of the invention, to target an oxygen range of from 0.5 to 2.0 ppm when in addition to the selenium compound according to the invention other, oxygen-sensitive compounds such as trace elements or vitamins are present in the same compartment as the said selenium. In certain embodiments, an oxygen range of from 1.0 ppm to 2.0 ppm may be preferable for stably formulating compositions according to the invention.

In certain embodiments of the invention, the solution of the medical product of the invention comprises sodium selenite. In some embodiments, the solution of the medical product of the invention comprises selenous acid. In some embodiments, the solution of the medical product of the invention comprises selenium dioxide.

In one preferred embodiment, the solution of the medical product of the invention comprises sodium selenite which has a selective gas requirement for remaining stable over a prolonged time in such solution. It was surprisingly found that the presence of a headspace of oxygen over a solution comprising at least one selenium compound in the form of Se(IV) to maintain the dissolved oxygen (DO) in the solution a stable concentration of about 0.5 ppm to about 8 ppm, leads to the stabilization of sodium selenite, selenous acid and/or selenium dioxide in the solution which is otherwise protected from the interchange of gases with its surrounding, because it is generally expected that oxygen is involved in redox reactions and is often deleterious for macro- and micronutrient stability in solution. In particular, certain trace elements and vitamins have been reported to be sensitive to the presence or absence of oxygen when stored in sealed containers, such as in sealed flexible bags.

Consequently, the present invention is based on the finding that the presence of a controlled concentration of dissolved oxygen in a solution maintained by the headspace of the oxygen over the solution comprising, for example, sodium selenite, selenous acid and/or selenium dioxide alone or in combination with further sensitive trace elements, such as iodine and/or copper, leads to stabilization of these selenium containing compounds which are known to be unstable in solution and in particular when present in sealed medical nutritional products which are generally provided in oxygen-impermeable containers to avoid the above-mentioned redox reactions.

As mentioned before, while oxygen-permeable containers are known, such as used, for example, for Peditrace™, and which allow gas exchange between the interior of the container and the surrounding air, most parenteral products are provided in oxygen-impermeable containers due to the redox sensitivity of the nutritional components contained. Oxygen-permeable containers, on the other hand, will not provide for a defined, stable oxygen concentration which was found to be a prerequisite for providing long-term stability especially of a highly sensitive composition of various trace elements. In contrast, the oxygen levels are subject to changes based on, for example, temperature or height (pressure), and unfavorable conditions during, for example, sterilization, transport or storage may lead to the degradation and loss of a sensitive compound such as, for example selenium in its Se(IV) form, even if the container is then again stored at better suited conditions that lead to the replenishment of lost dissolved gas, such as oxygen, in the container thorough the oxygen permeable film.

In one embodiment, the headspace in the present invention refers to the space which is not filled with any liquid solution of the flexible container/multi-chamber container or an inert gas, such as nitrogen, and to the volume of gas in such space.

In one embodiment, applicant found surprisingly that a headspace of oxygen over a solution comprising at least one selenium compound in the form of Se(IV) when combined with an oxygen barrier film for the container can maintain the dissolved oxygen (DO) in the solution a stable concentration of about 0.5 ppm to about 8 ppm, leading to the stabilization of sodium selenite, selenous acid and/or selenium dioxide in the solution which is otherwise protected from the interchange of gases with its surrounding.

For the avoidance of doubt, the solution of the flexible container/multi-chamber container of the invention comprising at least one selenium compound in the form of Se(IV), which is preferably selected from the group consisting of sodium selenite, selenous acid and selenium dioxide, may also be referred to as "the selenium solution", "the solution comprising/containing selenium", or "the solution comprising/containing Se(IV)."

In the context of the present invention, the wording "stable" or "controlled" concentration of a dissolved gas means that the concentration of dissolved gas does not fall below a given threshold over the complete shelf-life of the product containing the medical solution comprising a component with a selective gas requirement. It does not mean that the concentration of the selective dissolved gas is the same at any time from production through end of shelf-life, but that its loss or consumption can be controlled in a way to maintain a certain minimum concentration throughout shelf-life.

For example, "a controlled concentration of dissolved oxygen in a solution of 0.5 ppm to 8 ppm" relates to a dissolved oxygen (DO) concentration that remains in the range of 0.5 ppm and 8 ppm throughout shelf-life of the medical product of the invention, wherein 8 ppm corresponds about to oxygen saturation of the solution of the invention. In other words, it is not necessary that the exact oxygen concentration of the solution in the medical product remains stable, but it is required that throughout shelf life the concentration does not drop below this range, namely below 0.5 ppm. Accordingly, in preferred embodiments of the invention, the DO concentration in the solution is at least 0.5 ppm DO.

In one embodiment of the present invention, the controlled concentration of dissolved oxygen in a solution of 0.5 ppm to 8 ppm is maintained by a headspace of oxygen over the solution in one chamber of the flexible container/multi-chamber container. In one embodiment, the chamber comprises the stable (and controlled) concentration of dissolved oxygen in a solution of 0.5 ppm to 8 ppm and the headspace of oxygen over the solution is sealed.

In certain embodiments, the dissolved oxygen (DO) in a Se(IV)-containing solution is at least 0.5 ppm during shelf life. In certain embodiments, the dissolved oxygen (DO) in the Se(IV)-containing solution does not fall below 0.5 ppm throughout shelf life of the medical product.

In one embodiment, the solution comprises equal or above 1 ppm dissolved oxygen (DO) or dissolved carbon dioxide.

In one embodiment, the solution is a sterilized solution, such as, for example, a terminally heat-sterilized solution.

In another embodiment, the solution comprises at least one compound which requires certain levels of oxygen for remining stable over a prolonged time and especially during sterilization and storage.

In preferred embodiments, the dissolved oxygen (DO) in the medical solution, such as the Se(IV)-containing solution, at the time of filling (and optionally sealing) of the solution in the flexible container/multi-chamber container and before sterilization is at least 6 ppm. In some embodiments, the dissolved oxygen (DO) concentration in the solution at the time of filling and before sterilization is from 6 ppm to 8 ppm (wherein 8 ppm corresponds about to the oxygen saturation level of the solution).

In preferred embodiments, an oxygen tight sealed chamber of the flexible container/multi-chamber container comprising the medical solution comprises a headspace of a gas composition comprising oxygen. In other words, in such embodiments, at least one of the chambers of the flexible container/multi-chamber container comprising the medical solution with a requirement for certain oxygen levels comprises additionally a volume of a gas composition comprising oxygen. It is understood that such an additional gas volume or "headspace" is a space or volume within a sealed chamber that is not filled with the solution, i.e. a volume filled with air/gas left at the top of a filled container before sealing.

As mentioned before, a headspace would generally be avoided or minimized to the extent possible regarding potentially unwanted interactions between the gas included therein (ambient air) and the liquid (or solid) content of the container (see, for example, US20030110736A1).

In contrast, in the context of the present invention such a headspace can be intentionally used and designed to be sufficient for stocking a gas, such as oxygen, for example via the ambient air, so that oxygen that has, for example, been lost through the container film material, i.e. the primary container, can be replaced. For example, dissolved oxygen (DO) in a solution can thus be maintained above 0.5 ppm throughout the intended shelf-life which is generally targeted to be at least 12 months, 18 months or 24 months depending on the typical surrounding temperature, which may be from about 15° C. to about 25° C., preferably from about 15° C. to about 30° C. Using a headspace according to the invention, i.e. providing for a sufficient gas reservoir including, for example ambient air or any other gas or gas mixture that might be lost or otherwise consumed in the solution of a gas-impermeable bag or a chamber but is required for the stability of a compound contained in such solution is a general principle which can be used also in connection with various compounds that require a certain level of gas, such as, for example, oxygen or carbon dioxide, for prolonged stability in situations where gas is lost from the chamber of a multi-chamber bag (MCB), e.g. through the primary container.

In some embodiments, the selective gas is oxygen. In such case, the gas composition in the headspace comprising oxygen may be ambient air, which comprises about 78% nitrogen, 21% oxygen, about 1% of other gases. However, in certain embodiments the gas composition in the headspace comprising oxygen may be an oxygen enriched gas composition that may even be composed of almost only oxygen, especially in cases where the headspace volume should be reduced. In certain embodiments, the gas composition of the headspace may comprise from about 10-about 100% oxygen, such as about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 42, about 44, about 46, about 48, about 50, about 54, about 58, about 62, about 66, about 70, about 75, about 80, about 85, about 90, about 95, about 96, about 97, about 98, or about 99% oxygen. As will be known to the skilled person, higher oxygen levels may not be recommended due to the danger of fire or explosion especially during production.

In case of ambient air, the volume of the headspace may be the same or higher than the normal headspace that remains in containers or compartments providing for medical solutions. According to the invention, the headspace may be in the range of from about 5% to about 100% of the volume of the solution containing a compound with selective gas requirements and which is included in at least one chamber of the flexible container/multi-chamber container of the present invention.

For example, in case of 25 ml of a selenium (IV) solution comprising, for example, about 70 µg of selenium (IV), the headspace of the ambient air may be 10 ml. However, in certain embodiments the volume of the headspace of the ambient air or oxygen may be in the range of greater than about 10%, about 15%, about 20%, about 25%, about 30%, about 35%, about 40%, about 45%, about 50%, about 60%, about 70%, about 80%, about 90% or about 100% of the volume of the selenium solution.

Generally, the volume of the headspace of a selective gas according to the invention may be in the range of from about 5% to 100%% of the volume of medical solution containing the compound having selective gas requirements, e.g. in the range of from 10% to 60%, such as about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 55, about 56, about 57, about 58, about 59 or about 60% of the volume of the medical solution.

For example, in case of 25 ml of selenium solution sealed in a chamber of the flexible container/multi-chamber container, the headspace of an ambient air or oxygen may be in the range of about 2.5 ml to about 22.5 ml, about 2.5 ml to about 20 ml, about 2.5 ml to about 17.5 ml, about 2.5 ml to about 15 ml, or about 2.5 ml to about 12.5 ml, preferably about 3-about 12 ml, such as about 3, about 4, about 5, about 6, about 7, about 8, about 9, about 10, about 11 ml or about 12 ml. The skilled person can calculate corresponding volumes of headspace based on this disclosure in case of other volumes of the selenium solution.

As disclosed herein, the volume of the headspace of a gas may be adjusted accordingly if a different gas composition is used. For example, in case of a gas with enriched oxygen content, a smaller headspace may be used, as is evident to the skilled person and can be calculated on the basis of the above ratios indicated for ambient air and/or by routine experimentation depending on the compound to be stabilized in the medical solution.

In certain embodiments of the flexible container/multi-chamber container of the invention, the headspace of an ambient air or oxygen and the dissolved oxygen (DO) in the solution stabilizes at least one selenium compound in the form of Se(IV) such as sodium selenite, selenous acid and/or selenium dioxide, alone or in combination with other trace elements, in the solution for at least three months when stored at a broad temperature range of between about 1° C. and about 50° C. Instead of sodium selenite, other salt forms may be used as well, such as potassium selenite, lithium selenite, calcium selenite or magnesium selenite. So, where sodium selenite is mentioned, it should be understood as a preferred example of such alternatives only. It was surprising and unexpected that comparative experiments could demonstrate that the listed selenium containing compositions were stabilized in solution during various temperatures tested in the range of from about 1° C. to about 50° C. for prolonged periods in an oxygen-impermeable flexible container, such as at least three months.

In certain embodiments, the headspace of an ambient air or oxygen and the dissolved oxygen (DO) in the solution according to the invention stabilize the sodium selenite, selenous acid and/or selenium dioxide alone or in the presence of other trace elements in the solution for at least three months when stored at up to about 40° C. Furthermore, in certain embodiments, the headspace of an ambient air or oxygen and the dissolved oxygen (DO) in the solution stabilize the sodium selenite, selenous acid and/or selenium dioxide alone or in the presence of other trace elements in the solution for at least six months when stored at up to about 40° C.

In further embodiments of the invention, the headspace of an ambient air or oxygen and the dissolved oxygen (DO) in the solution of the present invention stabilize the sodium selenite, selenous acid and/or selenium dioxide alone or in the presence of other trace elements in the solution for at least 6 months, preferably for at least 12 months, more preferably for at least 18 months, most preferably for at least 24 months.

In further embodiments of the invention, the headspace of an ambient air or oxygen and the dissolved oxygen (DO) in the solution of the present invention stabilize the sodium selenite, selenous acid and/or selenium dioxide alone or in the presence of other trace elements in the solution for at least 6 months, preferably 12 months, more preferably 18 months, most preferably 24 months, at a temperature of up to about 30° C.

In yet further embodiments of the invention, the headspace of an ambient air or oxygen and the dissolved oxygen (DO) in the solution of the present invention stabilize the sodium selenite, selenous acid and/or selenium dioxide alone or in the presence of other trace elements in the solution for least 6 months, preferably for at least 12 months, more preferably for at least 18 months, most preferably for at least 24 months, at a temperature of from about 18° C. to about 25° C.

In still further embodiments of the invention, the headspace of an ambient air or oxygen and the dissolved oxygen (DO) in the solution of the present invention stabilize the sodium selenite, selenous acid and/or selenium dioxide alone or in the presence of other trace elements in the solution for least 6 months, preferably for at least 12 months, more preferably for at least 18 months, most preferably for at least 24 months, at a regular storage temperature, including for example, but without limitation thereto, of temperatures of room temperature, varying from about 15° C.-about 30° C., more preferably about 18° C.-about 25° C., or storage in refrigerated conditions, such as from about 1° C. to about 10° C., preferably about 2° C. to about 8°C, or about 3° C. to about 7°C.

According to another embodiment of the invention, the selective gas may be carbon dioxide, which is another example for a selective gas that is required for the stability of a compound in a medical solution that may be located in a MCB wherein the various compartments have different requirements as to the carbon dioxide. Accordingly, the disclosure made herein and relating to oxygen can equally be applied to and is valid also for carbon dioxide.

According to one embodiment of the invention, the selective gas is carbon dioxide ($CO_2$). According to yet another embodiment the compound having a selective gas requirement is bicarbonate, e.g. sodium bicarbonate. Bicarbonate and carbon dioxide in an aqueous solution are connected via the following equation:

$$CO_2(aq) + 2 H_2O \rightleftharpoons H_2CO_3(aq) + H_2O \rightleftharpoons HCO_3^+(aq) + H_3O^+.$$

The loss or permeation of carbon dioxide from, for example, a sodium bicarbonate solution leads to an increase in sodium carbonate content and hence to increased pH levels. Furthermore, loss of carbon dioxide leads to a lowering of the desired content and/or availability of bicarbonate ions in the final admixed composition of the sodium bicarbonate component solution. The bicarbonate, however, is required in such medical solutions. Carbonates, in turn, tend to form calcium carbonate or other precipitates (e.g., with magnesium) over time, which is detrimental for medical solutions which are intended, for example, for administration to a patient. On the other hand, high amounts of dissolved carbon dioxide may not be desirable in another compartment of a MCB, as it could bring down the pH to values that are not beneficial for compounds located therein. Accordingly, the loss of carbon dioxide is to be avoided or controlled as best as is possible. It is also important to gain proper control over the extent of $CO_2$ migration from and between bicarbonate and other solutions, especially within a MCB. The improved control and limitation of the amounts of $CO_2$ gas which can escape or does escape from bicarbonate-containing solutions and compartments may also provide opportunities for eliminating the need for an over-wrap.

Known methods of gaining some control involve using gas-impermeable primary films and/or over-wraps. Since the volume occupied by the over-wrap material is necessarily greater than the volume of the flexible bag container containing the bicarbonate and other solutions, there is always a volume within the over-wrap material which can receive $CO_2$ gas escaping from the bicarbonate solution as such. As in the case of oxygen, carbon dioxide barrier materials can be used to limit the loss of carbon dioxide over the primary bag material, as well as any loss through the overpouch. The primary bag can therefore be designed to contain a nylon layer. Also, the overpouch can be made from or comprise nylon. For example, the overpouch can be a laminated film comprised of different layers: $Al_2O_3$, PVDC and nylon with adhesive layers in between and supported by a polypropylene co-polymer.

For example, in U.S. Pat. No. 7,491,411$B_2$, a multiple compartment flexible bag assembly is described which includes a first predetermined volume of an aqueous sodium bicarbonate solution contained in at least one of the multiple compartments and a second predetermined volume of an aqueous acid component solution contained in at least another of the multiple compartments. In this case, the aqueous acid component solution comprises an amount of dissolved carbon dioxide, which allows that, upon mixing of the bicarbonate component solution with the acid component solution, the bicarbonate solution is exposed to an environment of a $CO_2$-containing solution rather than a $CO_2$-free solution, and secondly that carbon dioxide can migrate across the packaging material from the acid component solution into a gas-impermeable over-wrap flexible bag, thereby limiting the amount of carbon dioxide which can migrate from the sodium bicarbonate component solution into said over-wrap flexible bag. However, in this case, both compartments tolerate and thereby leverage the presence of carbon dioxide.

According to the present invention, and in analogy to what has been described for a MCB wherein one compartment comprises a compound (e.g., sodium selenite or selenium dioxide) requiring higher dissolved oxygen levels, a headspace can be used to provide for a reservoir of carbon dioxide, specifically in cases where a second compartment cannot tolerate higher dissolved carbon dioxide levels and an approach as described in the prior art cannot be used.

It is an important advantage that a medical solution that comprises a compound having a selective gas requirement, especially when contained in one compartment of a MCB that otherwise contains formulations with different requirements, can be sterilized after preparation and packaging into a flexible bag prepared from an oxygen-impermeable material that may be sealed airtight and liquid tight without a significant loss of the compound provided therein such as in particular sodium selenite, selenous acid and/or selenium dioxide alone or in the presence of other components, such as, for example, further trace elements, vitamins, or a macronutrient such as glucose. For example, the present invention allows to stabilize sodium selenite, selenous acid and/or selenium dioxide in a separate dedicated chamber of a MCB but also, for example, in the glucose chamber of a multi-chamber bag for parenteral nutrition or a stand-alone glucose solution for parenteral nutrition, or a stand-alone medical solution comprising, for example, certain vitamin and/or trace elements.

In certain embodiments, the solution of the invention undergoes terminal heat sterilisation after preparation of and filling the solution into the flexible container. Sterilisation may occur prior to or after filling of the solution into the flexible bag of the medical product of the invention, wherein terminal sterilisation, specifically heat sterilisation of the filled and sealed flexible container is preferable.

It is highly preferable that the flexible container/multi-chamber container or the chambers of the flexible container/multi-chamber container containing the gas-requiring compound is impermeable for said gas. For example, where the gas is oxygen or carbon dioxide, an oxygen or carbon dioxide impermeable material should be used. For example, the flexible container/multi-chamber container or the chambers of the flexible container/multi-chamber container containing the selenium comprising solution may be made of a material which is having an oxygen barrier less than 5 $cc/m^2/day$, less than 4 $cc/m^2/day$, less than 3 $cc/m^2/day$, less than 2 $cc/m^2/day$, less than 1 $cc/m^2/day$, and preferably less than 0.5 $cc/m^2/day$.

As mentioned before, a lower gas barrier should be accompanied by a larger headspace and/or a higher concentration of the selective gas. A higher gas barrier of the film material may allow to reduce headspace volume and/or the concentration of the selective gas.

Any ports should preferably be attached or sealed into the compartment which contains a headspace according to the invention in a gas tight manner, and/or should be gas impermeable ports to avoid the loss of selective gas over such port. A certain loss of, for example, oxygen through the port seals can be addressed according to the invention with an appropriate headspace used as a reservoir of e.g. oxygen to assure the stability of the relevant compound over the intended shelf-life. In certain embodiments, the chamber comprising the solution containing selenium comprises a port that is oxygen impermeable. In certain embodiments, the flexible container according to the invention that has at least two compartments does not have any ports attached to the compartment containing a medical solution comprising a compound with selective gas requirements.

Sterilisation of the present invention may be done by a terminal heat sterilisation process but also by using terminal filtration, gamma irradiation or any other sterilization technique. Also, the solution of the flexible container/multi-chamber container of the invention may be filled into the flexible container/multi-chamber container by an aseptic filling process ensuring that no contamination of the essentially sterile solution occurs during filling and before sealing of the flexible bag. In some embodiments, the solution may have been sterilized, but is not necessarily sterile. For example, a sterilisation treatment may have been conducted, but an absolute sterility may not be achieved and/or required.

In further embodiments, the concentration of dissolved oxygen (DO) in the solution is equal or above 0.5 ppm, more preferably equal or above 1.0 ppm. In certain embodiments, the concentration of the dissolved oxygen (DO) in the solution is not higher than 4 ppm. In certain embodiments the dissolved oxygen (DO) in the solution is higher than 0.8 ppm and not higher than 2 ppm.

In certain embodiments of the invention, the concentration of dissolved oxygen (DO) in the solution may be any value in the range of about 0.5, about 0.75 or about 1 to about 2 ppm or about 0.5, about 0.75, about 1 or about 2 to about 8 ppm, such as about 0.5, about 0.75, about 1, about 1.5, about 2, about 2.5, about 3, about 3.5, about 4, about 4.5, about 5, about 5.5, about 6, about 6.5, about 7, about 7.5 or about 8 ppm. The indicated ranges include the noted endvalues. Ranges comprising any combination of disclosed values are considered as embodiments of the invention.

In some embodiments, the concentration of dissolved oxygen (DO) in the solution maintained by the headspace of an ambient air or oxygen is equal or above 0.5 ppm, more preferably equal or above 1.0 ppm, throughout shelf life of the medical product.

In some embodiments of the invention, the dissolved oxygen (DO) in the Se(IV) containing solution maintained by the headspace of an ambient air or oxygen is at least 0.5 ppm throughout shelf life of the medical product of the invention. In some embodiments, the dissolved oxygen (DO) concentration in the solution maintained by the headspace of an ambient air or oxygen can decrease during shelf life but remains above 0.5 ppm. For example, it is preferable that the dissolved oxygen (DO) concentration of the solution is above 6 ppm at the time of filling of the solution into the flexible container and before sterilization. During sterilization and storage, the dissolved oxygen (DO) concentration may decrease over time but remains above 0.5 ppm throughout shelf life.

In certain embodiments of the flexible container/multi-chamber container of the invention, the concentration of the dissolved oxygen (DO) in the solution at the time of filling and preferably sealing of a chamber of the flexible container/multi-chamber container comprising the solution is at least 6 ppm.

In certain embodiments, it may be possible that the dissolved oxygen (DO) concentration in the solution decreases within the medical product after filling, sealing and sterilization and during shelf life of the product, even if the chamber comprising the solution is completely oxygen impermeable. In some embodiments, the oxygen of the solution may be consumed during shelf life, potentially by slow chemical reactions such as oxidation or degradation within the chamber over time, and therefore the oxygen concentration may decrease. Therefore, it is preferable that at the time of filling and sealing a medical solution according to the invention within a chamber of the flexible container/multi-chamber container, the dissolved oxygen (DO) concentration is at least 6 ppm, such as in the range of 6 ppm to 8 ppm. Such a high dissolved oxygen (DO) concentration at the time of filling and sealing ensures that during shelf life of the product the dissolved oxygen (DO) concentration remains stably above 0.5 ppm, meaning that even if oxygen consumption and or loss through the film material in the chamber occurs, the DO concentration does not sink below 0.5 ppm.

In certain embodiments, a flexible container/multi-chamber container with selective dissolved gas content for stabilizing at least one micronutrient of a medical product, the flexible container comprising: a solution (i.e., sealed in a chamber of the flexible container/multi-chamber container) comprising the at least one micronutrient such as at least one selenium compound in the form of Se(IV) as disclosed herein; and a headspace (i.e., sealed in a chamber of the flexible container/multi-chamber container) of a gas such as oxygen as disclosed herein.

In some embodiments, a sealed chamber of the flexible container/multi-chamber container comprising the solution comprising at least one selenium compound in the form of Se(IV) additionally comprises a headspace of a gas composition comprising oxygen.

In preferred embodiments, a flexible container/multi-chamber container or a chamber thereof which comprises the solution containing at least one selenium compound in the form of Se(IV) additionally comprises a headspace of a gas composition comprising oxygen, and the sealed chamber is oxygen impermeable, and the dissolved oxygen (DO) in the solution at the time of filling and preferably sealing of the chamber is at least 6 ppm. It was shown, that in such embodiments the dissolved oxygen (DO) in the solution is or remains equal or above 0.5 ppm throughout shelf life of the medical product.

It is a great advantage that a content of dissolved oxygen (DO) maintained by the headspace of an ambient air or oxygen according to the invention is suitable for stabilizing the selenium containing compounds alone and especially also in combination with other sensitive trace elements in the context of the medical product of the invention since such dissolve oxygen (DO) concentrations can be easily established without complicated technical instrumentation or manipulation of the solution.

It will be readily understood by the skilled person that other parameters may also have to be adjusted to further improve the stability of a compound that, for remaining stable in a medical solution over a prolonged time, have a selective gas requirement, such as, for example, selenium in the form of Se(IV). For example, pH may have to be adjusted and/or incompatibilities with other potential compounds in the formulation will have to be respected.

For example, a solution comprising selenium in the form of Se(IV), such as, for example, sodium selenite or selenium dioxide, may in addition have an acidic pH, preferably in the range of from about 1 to about 4, more preferably from about 2 to about 3.5, more preferably from about 2.5 to about 3.2. However, for prolonged stability the dissolved oxygen content will be of critical importance. Still, it is a particular advantage of the solution of the present invention that sodium selenite, selenous acid and/or selenium dioxide are stable in the presence of from about 0.5 to about 8 ppm dissolved oxygen (DO), and specifically also in the presence of from about 0.8 ppm to about 4 ppm dissolved oxygen (DO) or in the presence of from about 1 ppm to about 2 ppm, not only at about neutral pH in the range of about 7 to about 7.5, but also at acidic pH. The selenium in the solution of the flexible container/multi-chamber container according to the invention is in particular also stable at acidic pH, such as a pH value in the range of about 1-about 4, about 1.5-about 3.5, about 1.8-about 3.2, about 2-about 3, about 2.1-about 2.9, about 2.2-about 2.8, about 2.3-about 2.7, about 2.4-about 2.6 and about 2.5. The indicated ranges include the noted end-values. Ranges comprising any combination of disclosed end-values are considered as embodiments of the invention.

The stability at such acidic pH conditions is important, in particular if the solution also includes other trace elements that may not be stable at neutral pH, but only under acidic conditions. This is in particular the case for iodide (I), which has been reported to be more stable in solutions with acidic pH. However, this may also be the case for nutritional solutions comprising one or more of the trace elements copper (Cu), zinc (Zn), iron (Fe), manganese (Mn), chromium (Cr), fluoride (F) and molybdenum (Mo).

As another example, the stability of a solution comprising selenium in the form of Se(IV), such as, for example, sodium selenite or selenium dioxide, may be further enhanced by the presence of certain acids, such as, for example organic acids in the form of malic acid, tartaric acid, citric acid, maleic acid, and fumaric acid, and more preferably malic acid, wherein the concentration of the organic acid is preferably in the range of from about 100 mM to about 400 mM, preferably from about 190 mM to about 220 mM, and more preferably about 200 mM.

In another aspect, the present invention relates to a multi-chamber container with selective dissolved gas content in one chamber of the multi-chamber container for stabilizing at least one micronutrient of a medical product, the multi-chamber container comprising: a first chamber comprising a carbohydrate formulation; a second chamber comprising an amino acid formulation; a third chamber comprising a lipid formulation; and a fourth chamber comprising: a solution comprising the at least one micronutrient; and a headspace of the gas.

The present invention is directed to a sterilized solution within a multi-chamber container with selective dissolved gas content for stabilizing at least one micronutrient of a medical product comprising a solution provided in an oxygen-impermeable flexible container comprising at least one compound selected from the group comprising or consisting of sodium selenite, selenous acid and selenium dioxide, characterized in that the solution comprises about 0.5 ppm to about 8 ppm dissolved oxygen (DO) at about 20° C. to about 25° C.

In the context of the invention, the solution within the multi-chamber container preferably made from an oxygen-impermeable material (e.g., any material having an oxygen barrier less than 2 cc/m²/day, less than 1 cc/m²/day, preferably less than 0.5 cc/m²/day), comprises at least one compound selected from the group consisting of a selenite salt, e.g. sodium selenite, selenous acid and selenium dioxide, characterized in that the solution comprises about 1 ppm to about 8 ppm dissolved oxygen (DO).

Sodium selenite is the inorganic compound with the formula $Na_2SeO_3$. This salt is a colorless solid. The pentahydrate $Na_2SeO_3(H_2O)_5$ is the most common water-soluble selenium compound. Selenous acid (or selenious acid) is the chemical compound with the formula $H_2SeO_3$. Structurally, it is more accurately described by $H_2SeO_3$. It is the principal oxoacid of selenium; the other being selenic acid. Selenium dioxide is the chemical compound with the formula $SeO_2$ and is a colorless solid. It is one of the most frequently encountered compounds of selenium.

In some embodiments, the at least one micronutrient is at least one selenium compound in the form of Se(IV), and the dissolved gas is dissolved oxygen (DO).

In some embodiments, the at least one selenium compound is selected from the group consisting of sodium selenite, selenous acid and selenium dioxide.

In some embodiments, the at least one selenium compound is sodium selenite or selenium dioxide.

In some embodiments, the multi-chamber container of the present invention has at least two, at least three, at least four, at least five or at least six chambers. In some embodiments, the headspace setting of the multi-chamber container may be applicable in certain existing multi-chamber containers having at least two, at least three, at least four, at least five or at least six chambers.

For example, U.S.2009/0166363A1 (Baxter) discloses a multi-chamber bag (MCB) which has at least a fourth chamber (see claim 20). EP790051A1 (B. Braun) shows a four Chamber Bag including also a smaller chamber. EP2568947A1 (B.Braun) shows a three chamber bag with port tubes for filling from one side. U.S. Pat. No. 8,343,128B2 (Otsuka) shows a configuration with a small chamber. U.S.5,267,646A (Otsuka) includes another example for inclusion of small chambers which may contain specialty compounds (i.e., drugs, TE) with certain requirements as to the gas level/presence.

In some embodiments, the multi-chamber container of the present invention comprises at least five chambers.

In certain embodiments the multi-chamber container of the present invention comprises either five chambers or six chambers.

In certain embodiments, the solution of one chamber (e.g., the fourth chamber) of the multi-chamber container comprises equal or above 0.5 ppm dissolved oxygen (DO) maintained by the headspace of an ambient air or oxygen throughout shelf life of the medical product.

In certain embodiments, the solution of the fourth chamber of the multi-chamber container comprises from about 0.5 ppm to about 8 ppm dissolved oxygen (DO) maintained by the headspace of an ambient air or oxygen.

In certain embodiments, the solution of the fourth chamber of the multi-chamber container comprises equal or above 1 ppm dissolved oxygen (DO) maintained by the headspace of an ambient air or oxygen.

In embodiments of the invention, the solution of the fourth chamber of the multi-chamber container is a sterilized solution. In the context of the invention, the term "sterilized" relates to a solution that has undergone a process of sterilization. Sterilization refers to any process that eliminates, removes, kills, or deactivates all forms of life (in particular referring to microorganisms such as fungi, bacteria, viruses, spores, unicellular eukaryotic organisms such as *Plasmodium*, etc.) and other biological agents like prions present in a specific surface, object or fluid, for example food or biological culture media. Sterilization can be achieved through various means, including heat, chemicals, irradiation, high pressure, and filtration. Sterilization is distinct from disinfection, sanitization, and pasteurization, in that those methods reduce rather than eliminate all forms of life and biological agents present. After sterilization, an object is referred to as being sterile or aseptic.

According to certain embodiments of the invention, sterilization may be done by heat. According to another embodiment of the invention, sterilization involves heating under pressure in the presence of water to generate steam; this method is recommended by various pharmacopeias. Generally, the steam sterilization may be performed in an autoclave and can be used for drug products, medical devices, plastic bags and other single-use equipment, glass containers, surgical dressings and more.

Other methods encompass sterilization with moist heat. Sterilization can also be achieved via dry heating. Much higher temperatures)(180-200° C. are required for this method. Dry heating is commonly used to sterilize glassware, metal and other surfaces.

Exposure to radiation is another sterilization method used throughout the industry. Gamma radiation is the most common, though other options include infrared and ultraviolet radiation and high-velocity electrons. Radiation is typically used for the sterilization of single-use components/systems, but it can be used for packaged drug products.

Treatment with gases may also be a sterilization alternative. Such gases include ethylene oxide, formaldehyde, glutaraldehyde, propylene oxide, hydrogen peroxide and chlorine dioxide. This method may be more commonly used to sterilize clean-room suites. Sterilization via filtration is the only option if the other processes are not suitable for the specific product or component. In filtration, the final drug product solution is passed through a filter that has been produced under aseptic manufacturing conditions and designed with appropriate pore sizes/surface chemistries that remove bacteria via size exclusion, entrapment, electrostatic attraction and other modalities.

In certain embodiments, the concentration of dissolved oxygen (DO) in the solution of the fourth chamber of the multi-chamber container (e.g., maintained by the headspace of an ambient air or oxygen) at the time of sterilization is at least 6 ppm.

In certain embodiments, the volume of the headspace of an ambient air or oxygen is from about 5% to about 100% of the volume of the solution in the fourth chamber of the multi-chamber container.

In certain embodiments, the volume of multi-chamber container is about 35% to 45% of the volume of the solution in the fourth chamber of the multi-chamber container.

In certain embodiments, the headspace of an ambient air or oxygen of the fourth chamber of the multi-chamber container stabilizes the at least one selenium compound for a time selected from the group consisting of at least 3 months, at least 6 months, at least 12 months, at least 18 months, and at least 24 months when stored at a temperature between about 1° C. and about 30° C.

In certain embodiments, the multi-chamber container is stored at a temperature between about 18° C. and about 25° C.

In the context of the present invention, the medical solution along with a headspace of a selective gas, such as ambient air or oxygen, is provided in one sealed chamber of the multi-chamber container. In certain embodiments of the invention, the solution along with a headspace of an ambient air or oxygen is contained and sealed in one chamber of the multi chamber container having at least two, at least three, at least four, at least five or at least six chambers.

Preferably, the seals around a compartment comprising a medical solution and a headspace according to the invention should be gas tight. Filling ports may also form a potential gas leak through which the required gas according to the invention may be lost from the medical solution. Care should therefore be taken to use gas-tight ports or to remove them after filling if they are not needed afterwards e.g. as a medical or injection port. According to one embodiment of the invention, As used herein, the term "flexible container" or "multi-chamber container," refers to a container or bag made of a flexible material, such as bags made from plastic films. The term does not encompass polymeric rigid or semi-rigid containers.

Flexible containers or bags of the invention can be made of materials comprising, without limitation, polyvinyl chloride (PVC), polypropylene (PP), polyethylene (PE), ethylene vinyl alcohol (EVOH), ethylene-vinyl acetate (EVA), polyethylene terephthalate (PET), and all possible thermoplastic elastomers copolymers, essentially any synthetic material suitable for containing the components to be administered including laminated materials.

Oxygen impermeable flexible containers are known in the art and are made of gas barrier films that block oxygen migration to the outside of the container. Different technologies have been developed in order to provide oxygen barrier to transparent films, such as polyolefin films or polyethylene terephthalate films. The main technologies are the following: (1) Coating with high barrier materials, generally inorganic oxide layers (e.g. SiOx or $Al_2O_3$); (2) Multilayer films, wherein an inner layer consists a barrier material such as EVOH, polyamide, aluminum, halogenated polyvinylidene such as PVDC, amorphous nylon or crystalline nylon or combination of both, copolymers of ethylene vinyl alcohol copolymer layer (EVOH), polyolefins, including combinations of two or more of the above layers, and wherein the outer layers consist of structural polymer (e.g. PE, PP or PET). For example, EVOH has one of the lowest oxygen permeability reported among polymers commonly used in packaging. By chemical structure, EVOH is a semi-crystalline copolymer of ethylene and vinyl alcohol monomer units.

In one embodiment, the flexible container or the multi-chamber container may be made of a material having a high oxygen barrier of less than 5 $cc/m^2/day$, less than 2 $cc/m^2/day$, preferably less than 1 $cc/m^2/day$, and especially preferably less than 0.5 $cc/m^2/day$ (30° C./70% RH).

The "oxygen transmission rate", also referred to as "OTR," is the steady state rate at which oxygen gas can permeate through a film. OTR is expressed as a volume of oxygen that penetrates a given area in a one-day period; $cc/m^2/day$ (or 24 h) measured at a standard temperature of 23° C., and 0% relative humidity (RH).

The disclosure therefore also provides for a flexible container, preferably a multi-chamber container for parenteral or nutritional formulations which may be prepared from any of the before-mentioned flexible films Generally, the skilled person can select an appropriate film with a sufficiently low gas barrier according to the invention, such as a low oxygen or carbon dioxide barrier. For example, the container may be in the form of a bag having one or multiple compartments or chambers. The container, such as a bag, may include at least two chambers, but may also contain three, four, five or six or more chambers, and in one preferred embodiment, two or three chambers or, in another preferred embodiment four, five or six chambers.

Suitable containers, including soft bags, typically are sterile, non-pyrogenic, single-use, and/or ready-to-use. The multi-chamber containers are particularly useful for holding a parenteral nutrition product for adults, children or neonates and can provide a carbohydrate formulation as disclosed herein in the first chamber, an amino acid formulation as disclosed herein in a second chamber, and a lipid formulation as disclosed herein in a third chamber of the container.

The multi-chamber container may include vertical chambers as disclosed in U.S. Patent Publication No. 2007/0092579. For example, the multi-chamber container may be configured as a bag that includes two, three, four, five or six adjacent chambers or compartments. If desired, frangible barriers or openable seals (e.g., peel seals or frangible seals) are used to separate the chambers of the multi-chamber container. Multi-chamber containers may also comprise three chambers for accommodating a lipid emulsion, a carbohydrate formulation and an amino acid formulation, and further comprise at least one, in certain embodiments two or three smaller chambers which contain, for example, vitamin formulations and/or trace element formulations. In one specific embodiment, the multi-chamber container of the invention has a first chamber containing the lipid emulsion according to the invention, a second chamber containing an amino acid formulation, a third chamber containing a carbohydrate formulation, a fourth chamber containing a vitamin formulation and a fifth chamber containing a trace element formulation.

A multi chamber container or multi chamber bag (MCB) as used in the context of the invention may be designed for the parenteral administration of its reconstituted content after admixing the formulations contained in the respective chambers. Such MCB may have 2, 3, 4, 5, 6 or more chambers. The chambers of said MCB may have the same size or may have different sizes to accommodate various compositions and volumes. The chambers may be designed to contain volumes of from, for example, about 1 to about 5 ml, from about 5 to about 10 ml, from about 10 to about 50 ml, from about 50 to about 100 ml, from about 100 to about 250 ml, from about 250 ml to about 500 ml, from about 500 to about 1000 ml, from about 1000 to about 1500 ml. The MCBs can be designed to have chambers which are located adjacent to each other. The chambers may have various shapes. The chambers can be oriented horizontally and/or vertically to each other. Certain small chambers can be designed to be located within another, larger chamber, wherein, for example, the small chamber which is located within another, larger chamber can be accommodated and fixed into said larger chamber by welding at least one edge of said small chamber in between the weld seam of the surrounding larger chamber.

The openable seals of the multi-chamber containers permit formulations to be separately stored and admixed/reconstituted just prior to administration thereby allowing storage in a single container of formulations which should not be stored as an admixture for an extended period of time. Opening of the seals allows communication between the chambers and mixing of the contents of the respective chambers. The outside seals of the multi-chamber container are strong seals that do not open under the fluid pressure supplied to open the weaker peel seals or frangible seals between the chambers. In some embodiments, the openable seals of the multi-chamber container may be designed to allow for the admixing or reconstitution of only selected chambers of the multi-chamber container, for example, the admixing of the lipid emulsion with the vitamin chamber and the amino acid chamber, if so desired.

The multi-chamber container may be provided with instructions explaining a desired order with which to open the peel seals, so that constituent fluids are mixed in a desired order. The unscaling strengths of the two or more peel seals may be varied to promote the opening of the seals in the desired order. For example, the unsealing strength of the peel seal to be opened first may be ⅓ to ½ of the unsealing strength required to open the peel seal to be opened second.

In some embodiments, the multi-chamber container comprises at least a first chamber containing a carbohydrate formulation, a second chamber containing an amino acid formulation, and optionally a third chamber containing a lipid formulation, optionally comprises electrolytes and/or vitamins in at least the first, second and/or third chamber. According to a specific embodiment, at least one chamber comprising sodium selenite, selenous acid and/or selenium dioxide further comprises a headspace of an ambient air or oxygen.

Carbohydrate formulations provide a supply of calories, typically in the form of glucose. In particular, the carbohydrate formulation provides an amount of carbohydrate sufficient to avoid adverse effects such as hyperglycemia that has been observed in patients receiving parenteral nutrition.

EXAMPLES

The invention is further described by the following examples. These are not intended to limit the scope of the invention but represent preferred embodiments of aspects of the invention provided for greater illustration of the invention described herein.

Example 1: Tests Performed with Oxygen Semi-Permeable and Oxygen Impermeable Barrier Films Test have been performed with two different films, an oxygen semipermeable-film and an oxygen impermeable film.

The semi-permeable film is a co-extruded film having the following structure: PP|Tie|PA|Tie|PP/SEBS/LLDPE. Therein, PP refers to polypropylene, PA refers to polyamide, SEBS refers to styrene-ethylene-butylene-styrene block copolymer, and LLDPE refers to linear low-density polyethylene. "Tie" refers to special adhesive polymers or "tie resins" which are typically polyethylene copolymers of polar and nonpolar repeat units and with or without functional reactive groups, which are used to improve adhesion between the main layers of the multi-layer film. The oxygen barrier of the film is provided by the polyamide layer (~50 cc/m$^2$/day). Corresponding films have been described, for example, in U.S.2010/0247935A1. The semipermeable film allows some oxygen to pass.

The oxygen-impermeable film is made from a coextruded polyolefinic material laminated to a polyester with a vapor deposit of silicon oxide coated with a barrier layer to provide an oxygen barrier, i.e. the oxygen barrier provided by this particular PET-SiOx is <0.5 cc/m$^2$/day. In the tests described in FIGS. 1 and 2 (FIGS. 2A and 2B), 1 dd/25 ml of sodium selenite was present at a pH of 3.0±0.2. 100 mM malic acid was present as well in a 50 ml mono-bag having one port-tube, wherein the bag was either made of semi-permeable or oxygen-impermeable material as described above.

After mixing, the respective solution was flushed with nitrogen to arrive at a dissolved oxygen (DO) of below 0.5 ppm. A headspace of 10 ml ambient air was left in the 50 ml bag. After filling the oxygen was allowed to reach saturation (about 8 ppm, see FIG. 1). The respective container was sealed and wrapped in an oxygen impermeable aluminum overpouch to which an oxygen absorber was added. The respective container was then submitted to moist heat sterilization.

Figure 2A:
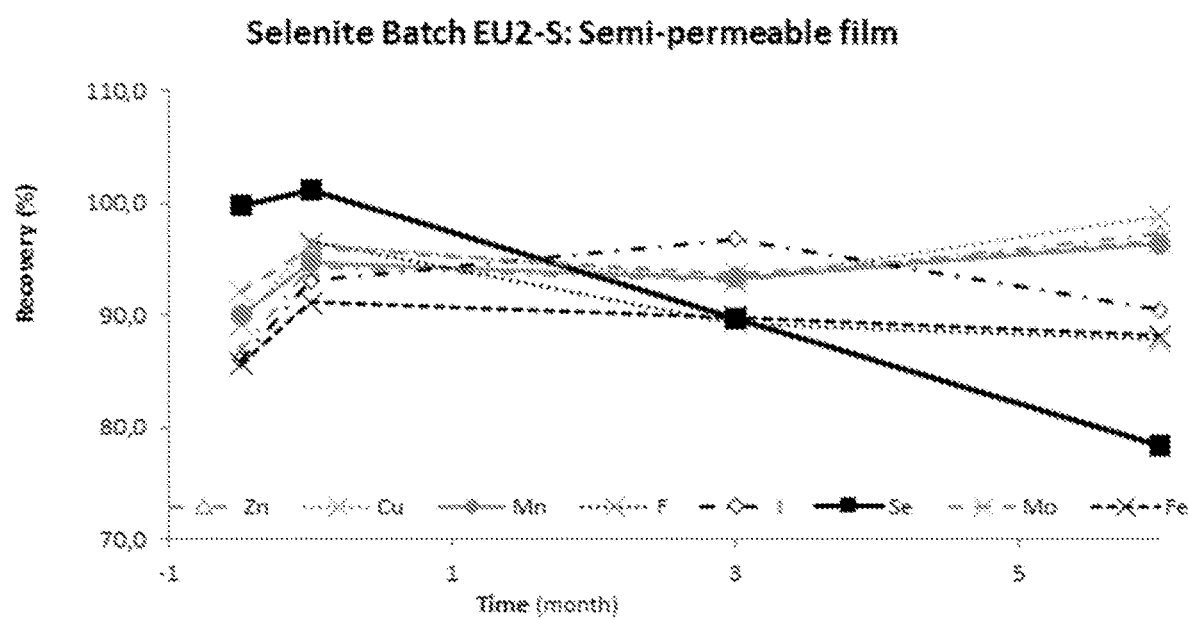
FIG. 2 (FIG. 2A and FIG. 2B) is a set of graphs showing selenite recovery levels of Selenite Batch EU2-S(semi-permeable film) (FIG. 2A) and Selenite Batch EU2-F (oxygen impermeable film)(FIG. 2B).
Figure 2B:
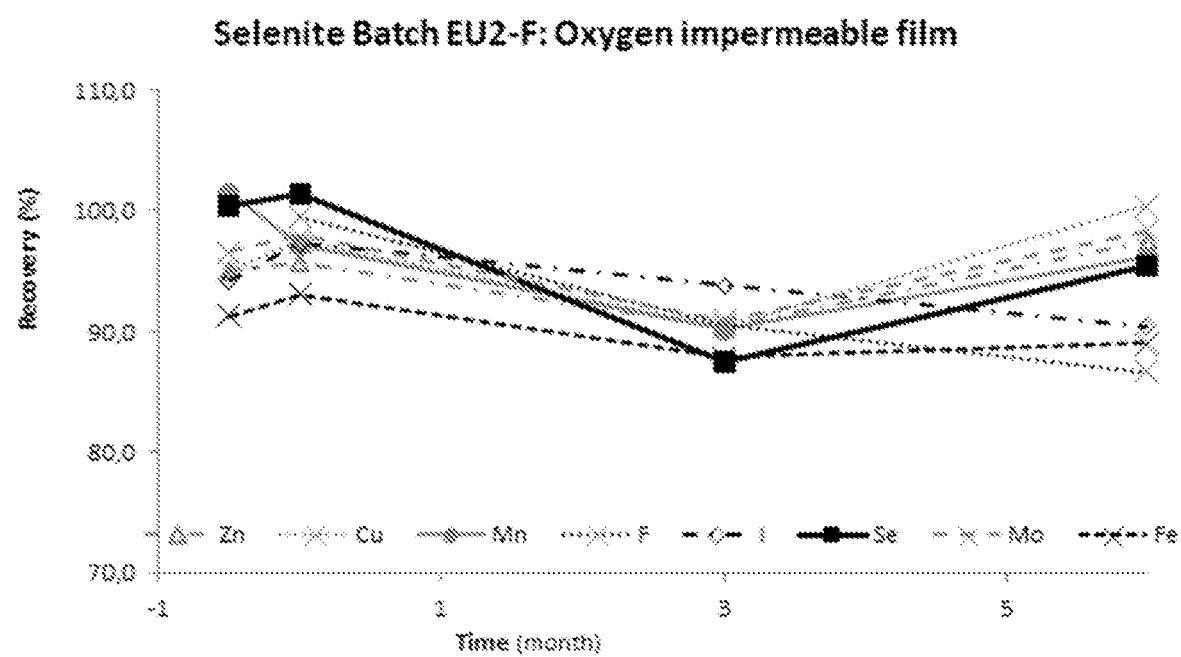

The following results were observed: It was found that selenite, in the EU-2S batch (semi-permeable), fell below 80% recovery after about 5 months (FIG. 2A). It can be concluded that oxygen is drawn from the solution because of the oxygen absorber present on the outer pouch and the presence of a semi-permeable primary film which allows oxygen to pass. In the EU2-F bag (oxygen-impermeable), this did not happen because of the oxygen barrier film (FIG. 2B). Selenite was retained and stayed above the threshold of 80% recovery. Therefore, an oxygen barrier film is advantageous to ensure stability of the selenite containing solution.

As shown in FIG. 1, the dissolved oxygen (DO) fell quickly, within about 3 months, from saturation to essentially 0 ppm dissolved oxygen (DO) in both cases but far quicker in the EU2S semi-permeable situation due to the effect of the oxygen absorber. After that time, the dissolved oxygen (DO) was essentially 0 ppm in both samples.

Accordingly, dissolved oxygen (DO) decreased even if an oxygen barrier film is used. It was found that the components in the solution, including other components (trace elements, malic acid), consumed the dissolved oxygen (DO), even though it was no longer lost by permeating through the film. In the presence of malic acid this was more pronounced. Without wanting to be bound by theory, it is assumed, that the redox potential in the solution favors the consumption of (reaction with) oxygen. However, as long as dissolved oxygen (DO) is maintained above 0.5 ppm, the selenite can be recovered with a rate of above 80% over 5 months. This was achieved by having a dissolved oxygen (DO), at the time of filling, of above 6 ppm, preferably between 6-8 ppm (essentially up to saturation).

Example 2: Relevance of Headspace

Figure 3:
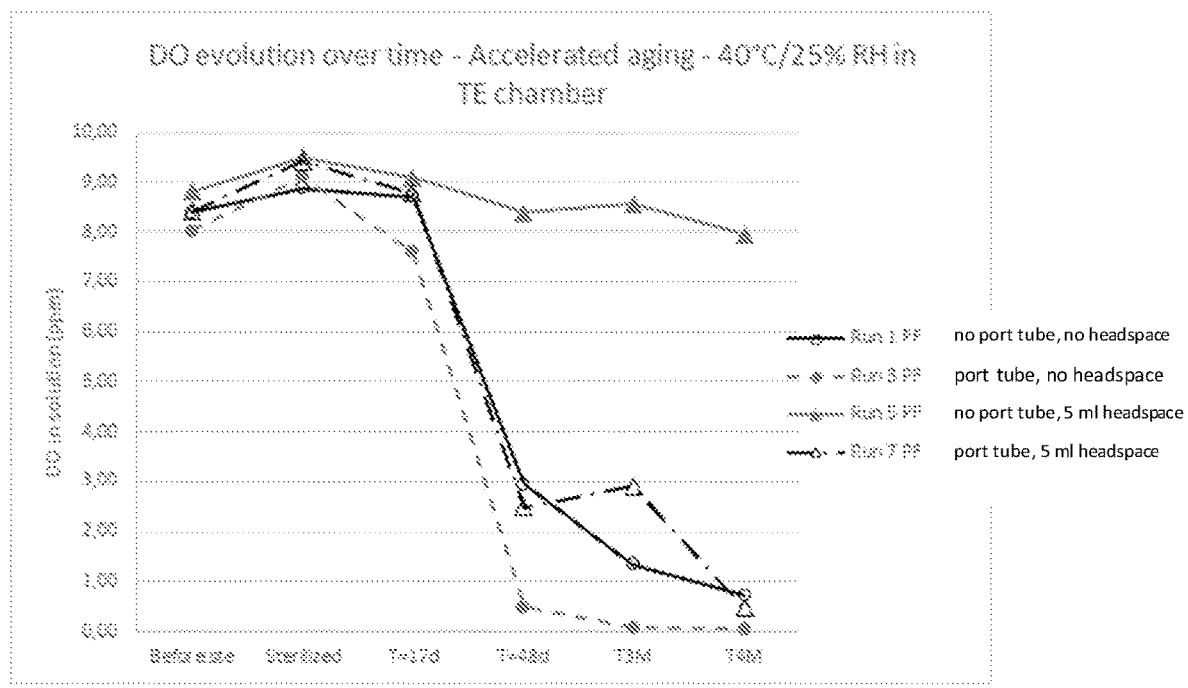
FIG. 3 is a set of graphs showing analysis of influence of the presence of a headspace and a port tube in combination with an oxygen-impermeable bag.

In this example, water was saturated with oxygen. The solution volume used was 15 ml. As shown in FIG. 3, it was found that without a headspace, even when the oxygen impermeable film was used, dissolved oxygen (DO) rapidly fell below the threshold of 0.5 ppm (in contrast to the above setup, where headspace was included).

It could thus be shown that the headspace filled with ambient air provides for a certain "oxygen stock" which replaces oxygen that is lost from the container. Oxygen from the headspace slowly gets dissolved in the solution until equilibrium is reached. Accordingly, the dissolved oxygen (DO) can be kept above 0.5 ppm over time if a headspace is present. Without headspace (filled grey circles), the selenite cannot be stabilized due to dissolved oxygen (DO) loss over time.

The port tube is another aspect which may contribute to dissolved oxygen (DO) loss, as the port tube must be sealed between the film layers and this portion of the seal is difficult to make completely oxygen tight. Accordingly, it is advantageous to improve the oxygen tightness of the port tube used in a setting as described herein, or, where possible, to completely remove the port tube. In FIG. 3, it becomes obvious that without headspace and without port tube (open black circles) the dissolved oxygen (DO) is higher over time compared to a port tube being present (closed grey circle), and that a headspace of 5 ml, for example, cannot fully compensate the loss over the port tube (open black triangle). Preferably, there is a headspace and no port tube, if possible, for stabilizing a selenite comprising solution in an oxygen barrier bag. In such setting, the dissolved oxygen (DO) can basically be maintained (filled grey triangle).

Figure 4:
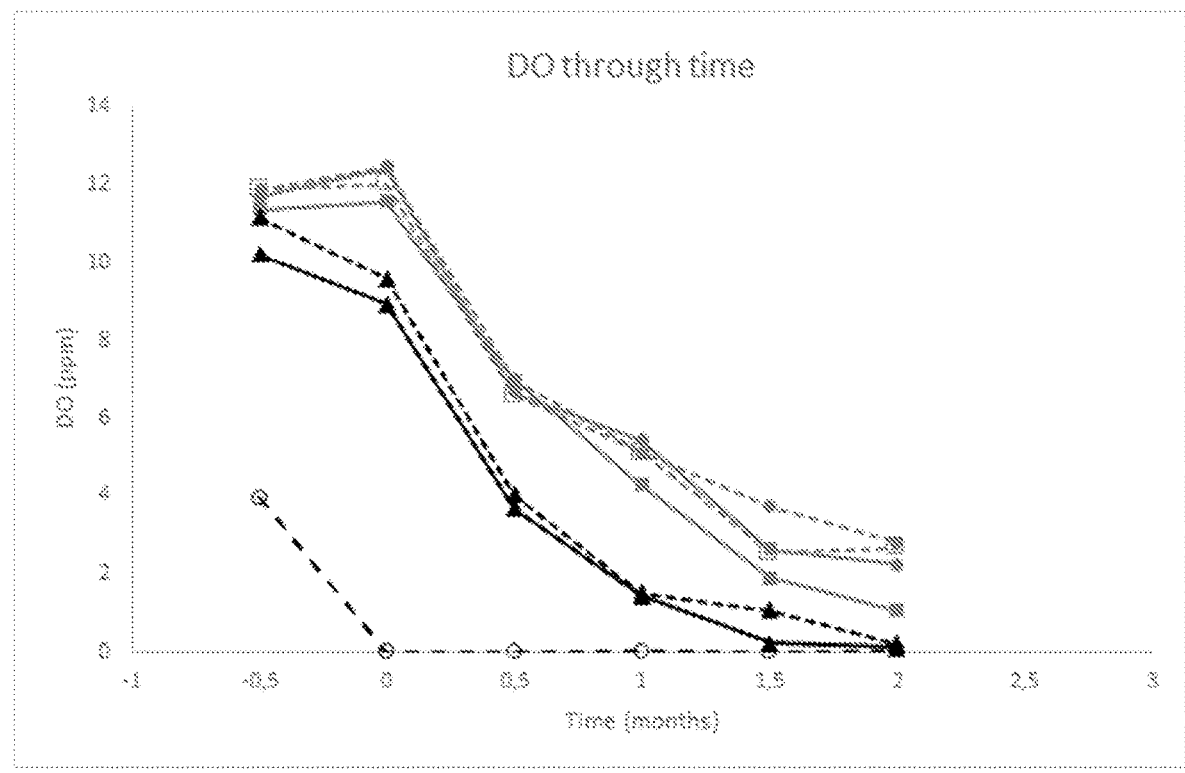
FIG. 4 is a set of graphs showing dissolved oxygen (DO) variation through time on the influence of the volume of the headspace.

FIG. 4 focuses on the volume of the headspace. As can be seen and as discussed above, a headspace is required for maintaining required DO levels in compositions where oxygen present in the solution at the time of filling is consumed by components present in the solution (DO is consumed by redox reaction in the solution, see open black circles, dashed line)or otherwise lost from the container. 2 ml headspace per 25 ml container/chamber volume or 15 ml solution is not fully sufficient either (black triangles). With 6 ml headspace the threshold of 0.5 ppm can about be met even if a port tube is present (grey square, continues line) and is fully sufficient if a port tube is absent (grey square, dashed line). Best results are obtained with a headspace of 10 ml per 15 ml solution of the chamber/container (filled grey circles, continuous line), even if port tube is present (filled grey circles, dashed line).

These results show that the headspace can be used as a reservoir for gas-requiring compositions and especially in setting involving different gas levels in a multi-chamber bag (MCB), i.e. in combination with low oxygen requiring chambers and formulation.

Example 3: Flexible Multi-Chamber Container Filled with Liquid Media that Shall have Selective Dissolved Gas Content to Guarantee Optimal Stability of the Content Liquid(s)

Flexible multi-chamber containers made from polymers films, for storing and keeping separated solutions are widespread particularly in the medical field and more particularly in parenteral nutrition.

In most cases, these containers are made from a polymer film with low or medium gas barrier properties. For parenteral nutrition (PN) products as for many other nutrition or drug products, the gas of interest mainly is oxygen. If, for stability reasons, one of the solutions shall be protected from oxygen, all the solutions will be usually prepared to be low in oxygen content. Even if only the sensitive solution is prepared to be low in oxygen, the system is rapidly moving to an equilibrium between the different chambers with no possibility to have selective gas content in the chambers.

In addition, the parenteral nutrition systems are usually packed in a secondary overwrap that is flushed with inert gas or that contains an oxygen absorber sachet, both playing a significant role in the rapid movement towards equilibrium between chambers and overwrap annular space.

This invention describes how the use of a particularly high barrier polymer film material, the removal of any potential component with low barrier properties and the addition of gas headspace to the system allows to maintain selective dissolved gas content in chambers over long term storage.

The present invention record describes a PN multi-compartment container with chambers containing nutriments that shall be protected from oxygen (e.g., amino acids, lipids, vitamins) and a chamber containing trace elements alone or mixed with other non-oxygen sensitive components, that shall contain a minimum of oxygen for the stability of Selenium in the form of selenite salts.

For the purpose of this invention, the plastic film material used to make the container shall have outstanding gas barrier properties. In the case of the parenteral nutrition, the gas of interest is oxygen. For this particular purpose, the permeability of oxygen shall be preferably lower than 0.5 cc/m²/ day (30° C./70% RH). This is achievable with a coextruded film containing a layer of Ethylene Vinyl alcohol copolymer (EVOH). However, PN products are usually moisture heat sterilized and EVOH material is partially losing its barrier upon moisture heat sterilization. This material is therefore not suitable.

The preferred choice is to use a laminated structure that is incorporating a substrate polymer layer with vapor deposition of silicon oxide or aluminum oxide. An additional barrier coating layer is sometimes added for better performance.

In the experiments shown as FIGS. 5-9, a structure laminated with the material GL-RD from TOPPAN was used. Three-chamber containers were manufactured with this particular film. The size of one chamber was reduced by sealing to fit with approximately 25 mL.

In a first experiment, chambers A and B of FIG. 5 were filled with respectively 200 mL and 300 mL water with a dissolved oxygen concentration below 1 ppm. The chamber C of FIG. 5 was filled with 25 mL water at ambient air (dissolved oxygen around 8 ppm).

After filling, the tubes were plugged, the bag was steam sterilized, overwrapped with an oxygen absorber sachet and then stored at 40° C.

Figure 6:
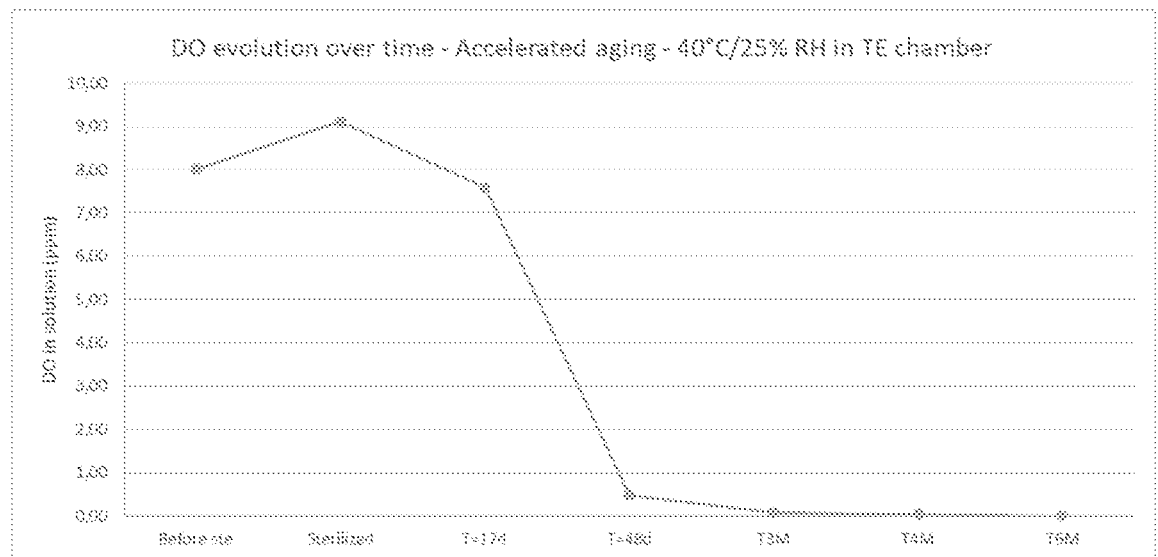
FIG. 6 is a graph showing dissolved oxygen (DO) variation through time at 40° C. for the Chamber C of the multi-chamber container of FIG. 5.

As shown in FIG. 6, after 17 days at 40° C., the dissolved oxygen concentration in the small chamber is still quite high (around 8 ppm), but after 48 days, it dropped below 1 ppm.

Figure 5:
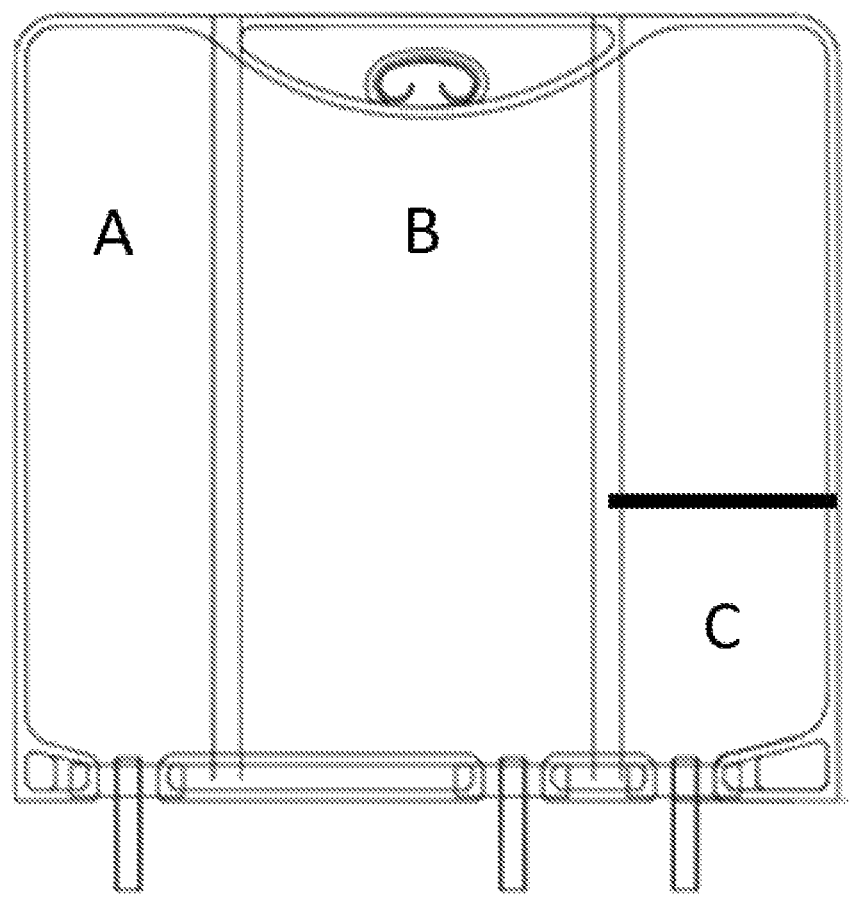
FIG. 5 is a picture showing an exemplary multi-chamber container.
Figure 7:
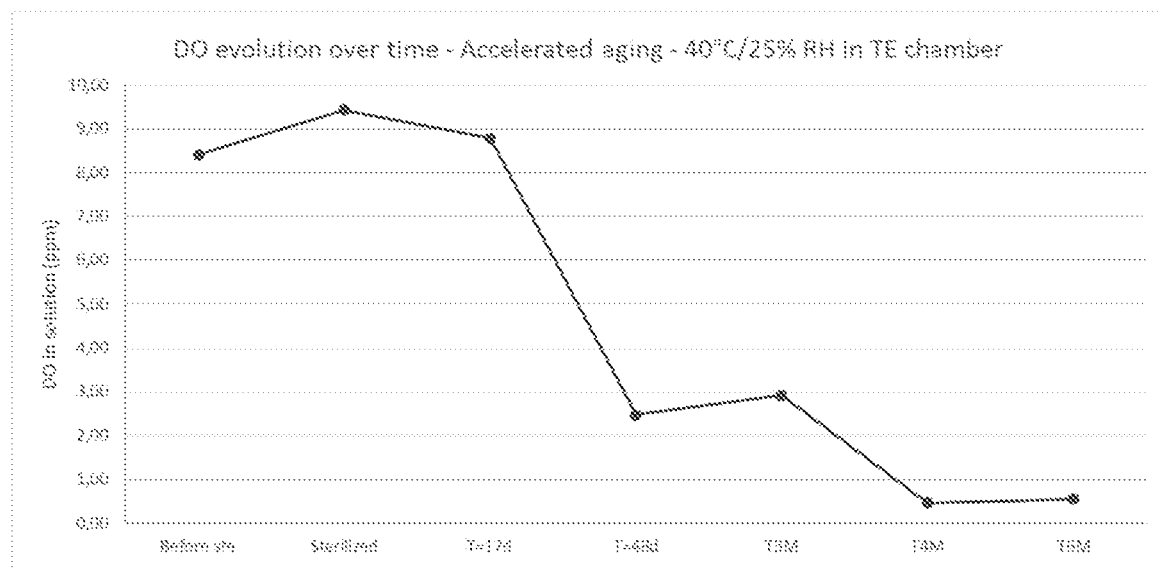
FIG. 7 is a graph showing dissolved oxygen (DO) variation through time at 40° C. for the Chamber C of the multi-chamber container of FIG. 5 after an air headspace of 5 mL was added to the Chamber C.

In the second experiment, an air headspace of 5 mL was added to the Chamber C of FIG. 5. As shown in FIG. 7, the drop of dissolved oxygen between is slower but it remains quite significant a value between 2 ppm and 3 ppm after 3 months' storage at 40° C.

The container shown on FIG. 5 is sealed with at least one filling port tube per compartment. These filling port tubes are manufactured by co-extrusion. Designing such tubes so that they would present a high oxygen barrier is not easy. As discussed above, the use of a layer of EVOH polymer is not a good choice as this polymer is losing its barrier properties during moisture heat sterilization. The addition of a PVDC layer is not desirable for sustainability reasons. The use of Nylon will only moderately improve the barrier.

The current tube formulation is not presenting any particular barrier properties and it is therefore assumed that the drop of dissolved oxygen in the small compartment results from the permeation of oxygen towards the filling tube wall.

Figure 8:
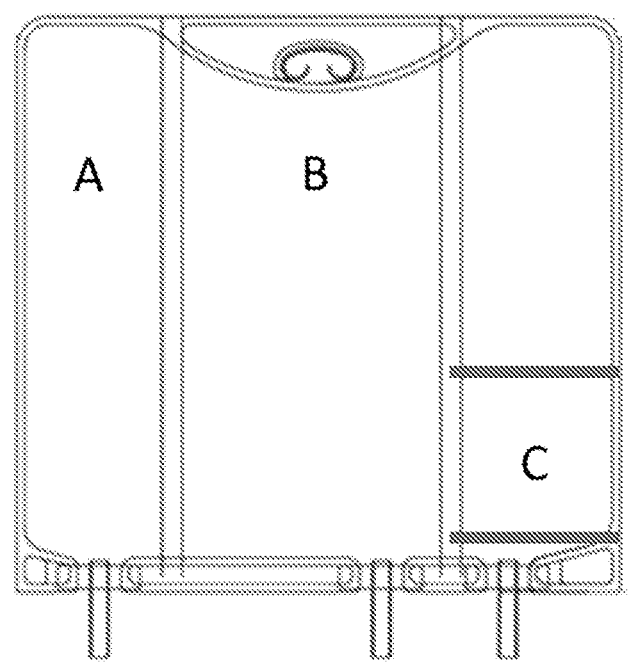
FIG. 8 is a picture showing another exemplary multi-chamber container, which is similar to that of FIG. 5, but a seal is added to isolate any filling tube from the Chamber C.

FIG. 8 is a picture showing another exemplary multi-chamber container, which is similar to that of FIG. 5, but a seal is added to isolate any filling tube from the Chamber C.

A third experiment was conducted with the Chamber C of the multi-chamber container of FIG. 8 filled with 25 mL of water and an additional air headspace of 5 mL, and with a seal added to isolate the tube from the Chamber C.

Figure 9:
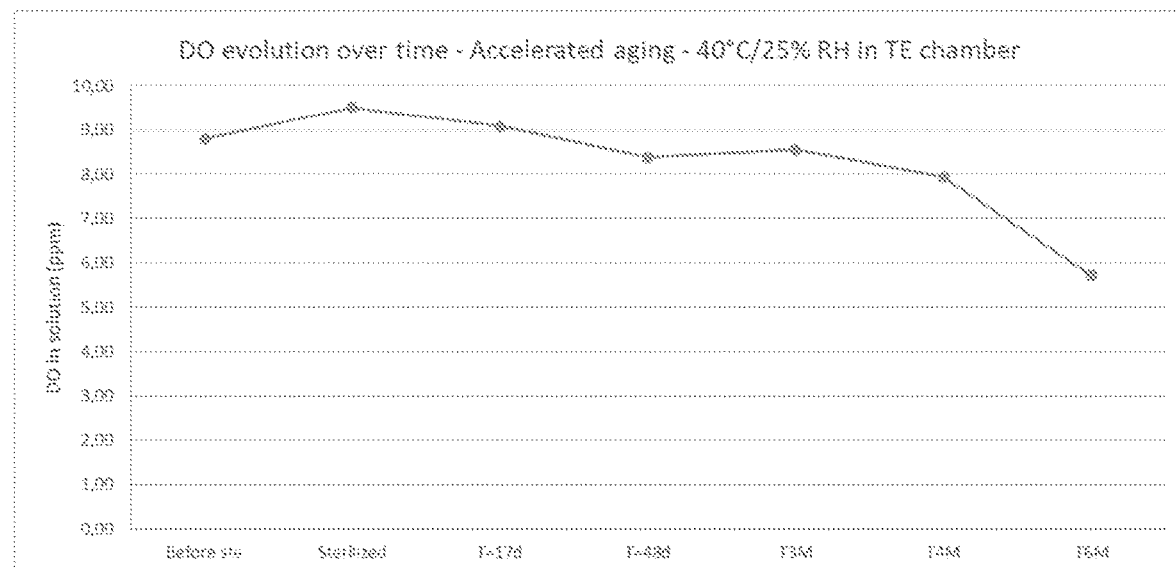
FIG. 9 is a graph showing dissolved oxygen (DO) variation through time at 40° C. for the Chamber C of the multi-chamber container of FIG. 8 and showing that the level of dissolved oxygen being still around 5 to 6 ppm after 6 months' storage at 40° C.

FIG. 9 shows the results of this third experiment with the level of dissolved oxygen being still around 8 ppm after 3 months' storage at 40° C., and about 6 ppm after storage for six months at 40° C.

The above results are showing that, despite the low dissolved oxygen in the other chambers and in the overwrap annular space, the use of a particularly high barrier polymer film material, the removal of the component with low barrier properties (filling tube) and the addition of gas headspace to the system allows to maintain a high dissolved oxygen content selectively in one chamber over long term storage.

Three-chamber bags are used above as illustrations, but this invention can be used also for any multi-chamber containers or bags, such as a five-chamber bag, a six chamber bag, a four-chamber bag or a two-chamber bag "amino acid/dextrose" with the trace elements or at least the Selenium in selenite form being in the dextrose chamber in an oxygen environment whereas the amino acid would remain in their chamber in an oxygen-free environment.

Alternatively, a primary film with no particular barrier properties can be used but the chamber that shall be with a different dissolved oxygen content shall then be protected. A well-known way to proceed is to cover that chamber by a peelable foil strip protecting this particular chamber from gas transfer.

This technology is used in two-chamber bag "solid/diluent" to protect the compartment containing the solid drug from moisture (e.g., Duplex container from BBraun). This process is however technically more complex, particularly for products that shall withstand a moisture heat sterilization.

Example 5: 6 Months' Accelerated Study

Figure 10:
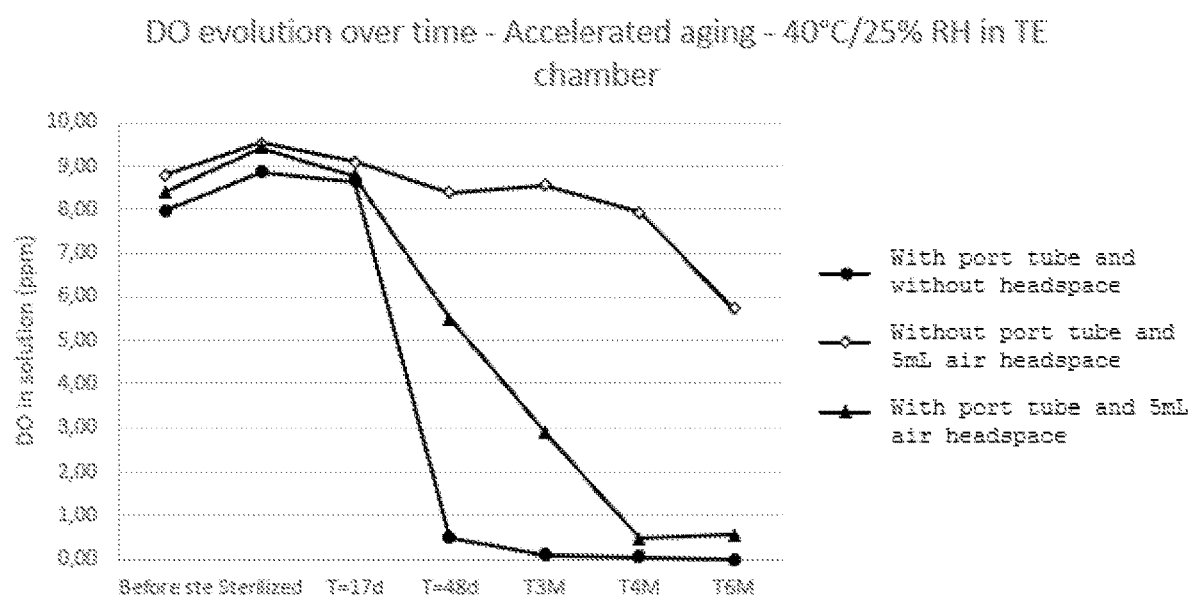
FIG. 10 is a set of graphs showing dissolved oxygen (DO) variation through time at 40° C. showing that the level of dissolved oxygen being still above 5 after 6 months' storage at 40° C. with a high barrier primary film, a small headspace of air (5 ml) and the removing of the port tube (Run 5).

FIG. 10 shows that the dissolved oxygen level in the trace element chamber with the very high barrier primary film, a small headspace of air (5 ml) and the removing of the port tube (seal & cut process)that should remain with a significant level of oxygen. As shown in Run 5 of FIG. 10, the dissolved oxygen level remains above 5 ppm after 6 months' storage at 40° C.

Figure 11:
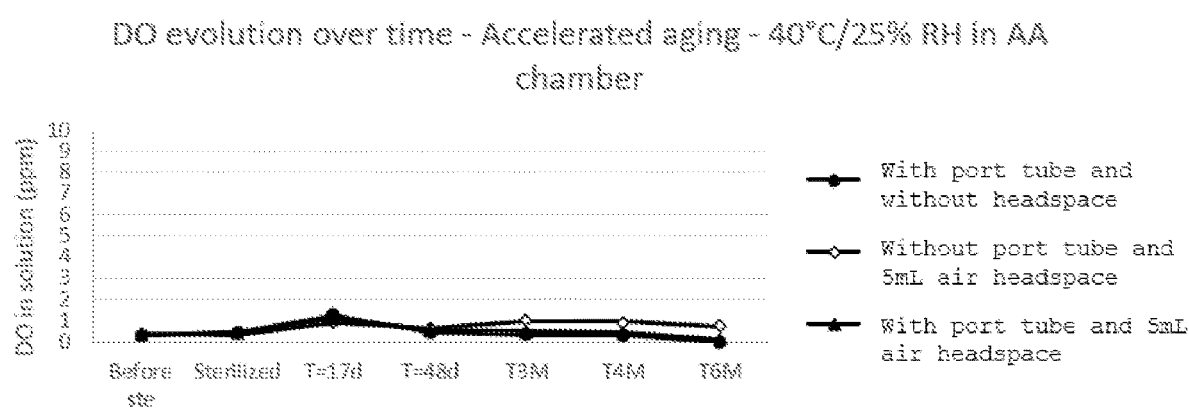
FIG. 11 is a set of graphs showing the stability of the low level of dissolved oxygen in the chambers that have been filled with a low dissolved oxygen media.

As comparison, FIG. 11 shows the stability of the low level of dissolved oxygen in the chambers that have been filled with a low dissolved oxygen media. As shown in Run 5 of FIG. 11, a similar level of dissolved oxygen to that before sterilization remains after 6 months' storage at 40° C.

Table II shows Dissolved $O_2$ in TE chamber (ppm) and Table III shows Dissolved $O_2$ in AA chamber (ppm). Specifically, Table II shows the development of DO in the trace element chamber, and Table III shows the development of DO in the amino acid chamber, to show that the approach can be used within an MCB and chambers with different oxygen requirements. In the AA chamber, the DO content is low at the time of filling, as the chamber and solution are generally flushed with nitrogen to bring down the oxygen content. If a highly oxygen impermeable film is used, this has to be done because less oxygen can be removed from e.g. the AA chamber by passing through the film and being captured by an oxygen absorber/scavenger which is placed in the overpouch. In the TE chamber, the oxygen content is pushed to about 8 ppm and remains relatively high as soon as a headspace reservoir with oxygen (e.g. ambient air) is available.

TABLE II

Dissolved $O_2$ in TE chamber (ppm)

| Configuration of the TE Chamber | Dissolved O2 in TE chamber (ppm) | | | | | | |
|---|---|---|---|---|---|---|---|
| | Before sterilization | Sterilized | T = 17 d | T = 48 d | T3M | T4M | T6M |
| With port tube and without headspace | 7.98 | 8.86 | 8.64 | 0.48 | 0.11 | 0.05 | 0.00 |
| With port tube and 5 mL air headspace | 8.80 | 9.52 | 9.09 | 8.38 | 8.56 | 7.94 | 5.73 |
| Without port tube and 5 mL air headspace | 8.40 | 9.43 | 8.78 | 5.48 | 2.91 | 0.46 | 0.55 |

TABLE III

Dissolved $O_2$ in AA chamber (ppm)

| Configuration of the TE Chamber | Dissolved O2 in AA chamber (ppm) | | | | | | |
|---|---|---|---|---|---|---|---|
| | Before sterilization | Sterilized | T = 17 d | T = 48 d | T3M | T4M | T6M |
| With port tube and without headspace | 0.31 | 0.428 | 1.25 | 0.44 | 0.34 | 0.31 | 0.01 |
| With port tube and 5 mL air headspace | 0.37 | 0.33 | 0.92 | 0.63 | 0.98 | 0.96 | 0.72 |
| Without port tube and 5 mL air headspace | 0.33 | 0.47 | 1.14 | 0.57 | 0.50 | 0.46 | 0.10 |

Example 6: Evaluation of Various Factors on the Stability of Selenite

A full factorial Design of Experiments (DoE) was developed to evaluate the impact of five factors on the stability of Selenite:

Container material: an interaction between Selenite and plastic bags material was previously highlighted. To evaluate this factor a neutral (gas impermeable) material i.e., glass bottles was used as a comparison to plastic bags.

pH of the solution: all previous studies were conducted at pH<3.5 to ensure stability of Fe. A comparison with a native pH >7 obtained by simple dilution of Selenite into MilliQ water allowed to evaluate the impact of this parameter.

Sterilization: the terminal heat sterilization conducted on samples may initiate degradative chemical reactions by heat exposure. Unsterilized VS sterilized samples were compared regarding Selenite stability to assess the impact of this process step.

Storage temperature: accelerated stability studies are classically conducted at 40° C. However, selenite might be sensitive to it and a comparison with samples stored at 5° C. was conducted.

Dissolved oxygen content: oxygen is involved in many redox reactions most of the time deleterious for macro and micronutrients (particularly vitamins). To assess the impact of this parameter on Selenite stability, solutions of Selenite were flushed either with oxygen (up to saturation at about 8 ppm) or with nitrogen (DO<0.5 ppm).

All combinations of factors were produced and stored under appropriate conditions for 6 months. They were then submitted to several tests to evaluate the impact of each factor on several responses.

The following readouts were performed in order to assess the impact of the factors listed above:

Se assay to evaluate the degradation of Selenium.

Visual inspection of the samples to detect any precipitate, particles or discoloration.

pH measurement to evaluate the evolution of sample pH after 6 months storage.

Dissolved oxygen measurement to evaluate the evolution of the dissolved oxygen after 6 months of storage.

Redox potential measurement as Selenite is engaged into different Se redox couples the information on redox potential of the solution might help to understand the stability of this element.

For almost all responses studied, a same group of samples presented a different behavior than the rest of them. Observations are detailed in Table IV below.

TABLE IV

Assessment of the different readouts visual inspection, pH, Dissolved oxygen, delta redox potential and Se assay for samples flushed with nitrogen and stored in plastic bags versus other samples (i.e. all samples flushed with oxygen + samples flushed with nitrogen and stored in glass bottles).

| Response | Samples flushed with Nitrogen and stored in plastic bags | Other samples i.e. all samples flushed with oxygen + samples flushed with nitrogen and stored in glass bottles |
| --- | --- | --- |
| Visual inspection | No particles nor discoloration but strong egg-smell at the opening of the overpouch | Particles dust like in the glass bottles. Nothing detected in plastic bags samples |
| pH | No significant variation of pH after 6 months storage | No significant variation of pH after 6 months storage |
| Dissolved oxygen | About 0 ppm of oxygen detected after 6 months | All samples present significant content of oxygen (>1.5 ppm) even samples in glass bottles flushed with nitrogen during manufacturing |
| Delta redox potential | Significant decrease of redox potential during the 5 minutes measure (up to −400 mV) witness of a reductive reaction | No significant variation during the 5 minutes measure or slight increase witness of a neutral or oxidative behaviour |
| Se assay | Significant degradation of Se (i.e. more than 10% degradation after 6 months) | No significant degradation of Se (i.e. +/−10% variation after 6 months) |

Figure 12:
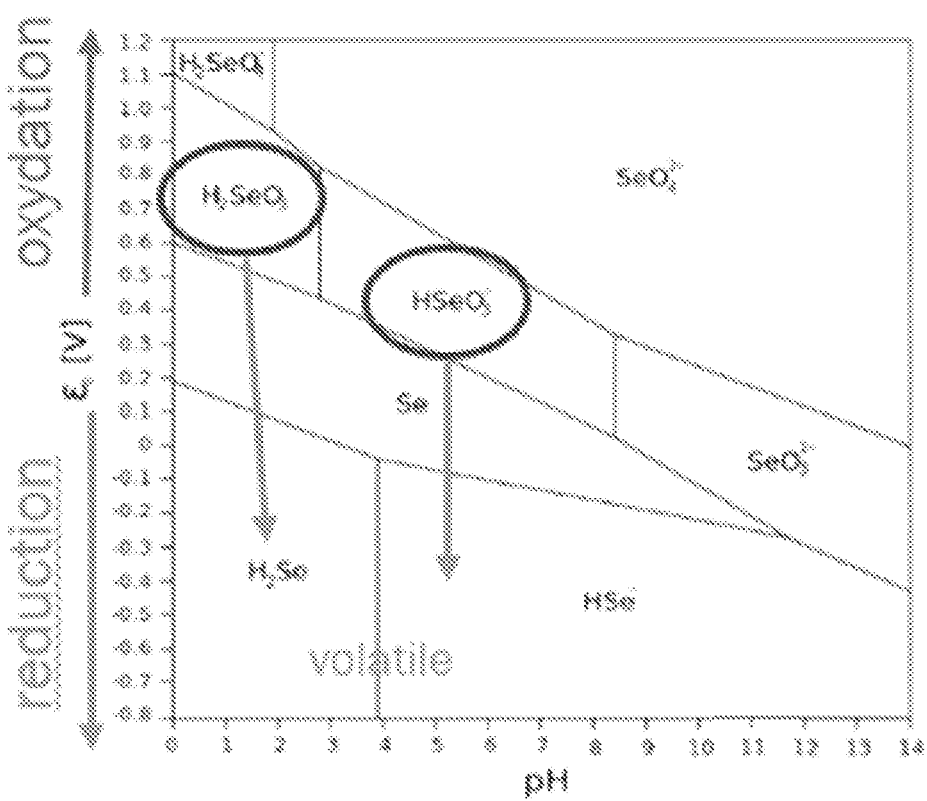
FIG. 12 is a pH/redox diagram showing the transformation of $SeO_3$ in these volatile species in a medium totally free of oxygen.

These observations allowed to conclude that in samples flushed with nitrogen and stored in oxygen-permeable plastic bags the degradation of selenium observed is most probably due to a reduction of Selenite $SeO_3$ in $H_2Se$/$HSe-$, a volatile form of Se known to present a bad smell similar to sulfuric gas. The pH/redox diagram presented in FIG. 12 illustrates the transformation of $SeO_3$ in these volatile species in a medium totally free of oxygen.

Example 7: Impact of DO on Selenium Stability

The impact of oxygen seems of major importance in the stability of Selenite. Indeed, the few amounts of oxygen that penetrates into the solution initially flushed with nitrogen but stored in glass bottles certainly blocked the reduction reaction and allowed to maintain the stability of $SeO_3$. To confirm this hypothesis, a regression test was performed between Se assay results and log(dissolved oxygen results). Only sterilized samples stored at 40° C. were considered as the sterilization and storage at high temperature seem to both increase the Se degradation. Indeed, most reaction kinetics are accelerated by heat explaining that samples not sterilized and kept at 5° C. for 6 months do not present a degradation as important as for samples sterilized and stored at 40° C.

Figure 13:
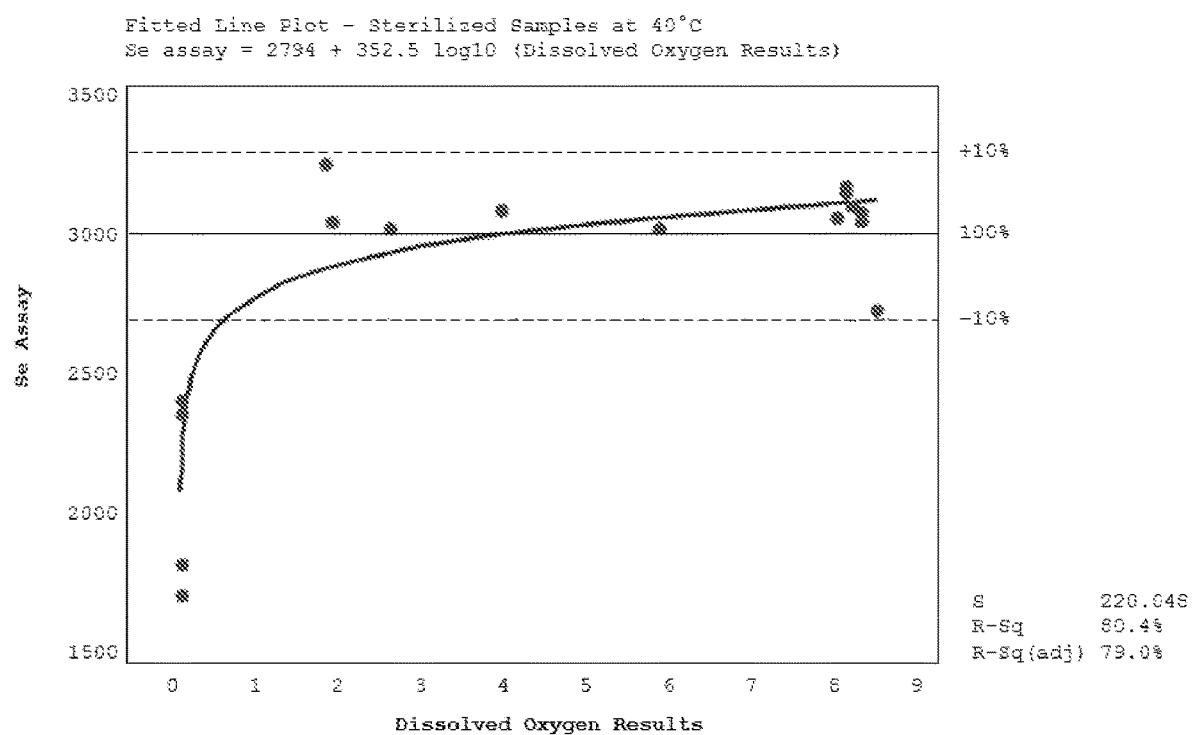
FIG. 13 is a graph showing a fitted line plot between Se dosage and log oxygen content.

The fitted line plot presented in FIG. 13 shows a 80% fit between Se dosage and log oxygen content. Considering a +/−5% analytical variability and the few samples used for this regression test it can be considered as significantly representative. Dissolved oxygen content is so the most impacting parameter and CQA (Critical Quality Attribute) in the stability of Selenium. As shown in the Figure, low oxygen amounts of around 0.5 ppm can be sufficient to ensure the stability of Selenite in solution, no saturation would be required.

The presence of oxygen promotes selenite stability. For comparison, the stability of a mix of other trace elements (i.e. Zn, Cu, Cr, Mo, Mn, Fe, I, F & Se) was evaluated at pH 2.2 with 200 mM of malic acid (to ensure iodide stability) and stored in a glass bottle (so containing about 3 ppm of dissolved oxygen). The solution was heat sterilized and stored 6 months at 40° C. or 5° C.(T6M 40° C. and T6M 5° C., respectively). Recovered concentrations of the respective trace elements after 6 months at the two temperatures are summarized in the Table V.

TABLE V

Initial (theoretical) concentration of the respective TE and the concentrations recovered after 6 months at 5° C. or 40° C. and corresponding percentage of the recovered TE are indicated.

| TE | Theoretical concentration µg/L | T6M 5° C. µg/L | % | T6M 40° C. µg/L | % |
|---|---|---|---|---|---|
| Zn | 203561 | 158347 | 77.8% | 171822 | 84.4% |
| Cu | 12057 | 9784 | 81.1% | 10504 | 87.1% |
| Mn | 2204 | 1838 | 83.4% | 1949 | 88.4% |
| F | 39959 | NA | 94% | NA | 88% |
| I | 4029 | 3167 | 78.6% | 3401 | 84.4% |
| Se | 2806 | 2446 | 87.2% | 2461 | 87.7% |
| Mo | 817 | 653 | 79.9% | 707 | 86.6% |
| Cr | 396 | 306 | 77.3% | 329 | 83.1% |
| Fe | 40116 | 31842 | 79.4% | 34190 | 85.2% |

For all TE, recoveries are around 80-90% at both temperatures. An excessive dilution might explain this lower than expected recoveries, but it is known that at 5° C. samples should be stable and so it can be considered as a reference. Comparison of the two samples shows that none of the TE was degraded significantly after 6 months storage at 40° C. It confirms the hypothesis that selenite stable in the presence of few ppm of dissolved oxygen. This presence of oxygen is not deleterious for the stability of the other TE.

It can be attested that oxygen introduction would not be a problem in manufacturing. For example, instead of flushing the solution with nitrogen as it was done so far, it can be kept under ambient air thereby allowing a sufficient amount of oxygen to be dissolved into the solution. However, to reproducibly adjust the dissolved oxygen content, the solution can also be flushed with nitrogen followed by a defined time and amount of flushing with oxygen containing gas. The oxygen content can be monitored at any time as an in-process control with methods known in the art. During filling, sterilization and storage steps, the dissolved oxygen can be maintained in the solution by using a bag material impermeable to oxygen. Such materials do neither allow any oxygen entering the bag nor being removed out of the bag (even in contact with an oxygen absorber). This way the oxygen would remain entrapped within the TE solution and avoid Se degradation all along the shelf life of the product.

The invention claimed is:

1. A multi-chamber container comprising a gas impermeable material and including solutions having different dissolved gas requirements, the multi-chamber container comprising:

(a) at least one first chamber including a headspace and containing a first solution comprising at least one selenium compound, and said headspace is filled with ambient air, oxygen enriched ambient air, or oxygen; and (b) at least one second chamber containing a second solution protected from oxygen.

2. A multi-chamber container comprising a gas impermeable material and including solutions having different dissolved gas requirements, the multi-chamber container comprising:

(a) at least one first chamber with a headspace and containing a first solution comprising at least one first compound requiring a first selective dissolved gas for stabilization, the at least one first chamber comprising said first selective dissolved gas in said headspace; and (b) at least one second chamber containing a second solution comprising at least one second compound requiring the absence of the first selective dissolved gas.

3. The multi-chamber container of claim 2, wherein the at least one first compound is a compound requiring at least about 0.5 ppm of oxygen for stabilization, and the first selective dissolved gas is oxygen.

4. The multi-chamber container of claim 3, wherein the first solution comprises equal or above 0.5 ppm dissolved oxygen (DO) throughout shelf life of the medical product.

5. The multi-chamber container of claim 3, wherein the first solution comprises from about 0.5 ppm to about 8 ppm dissolved oxygen (DO).

6. The multi-chamber container of claim 3, wherein the first solution comprises equal or above 1 ppm dissolved oxygen (DO).

7. The multi-chamber container of claim 3, wherein the concentration of dissolved oxygen (DO) in the solution at the time of sterilization is at least 6 ppm.

8. The multi-chamber container of claim 2, wherein the at least one first compound is a compound requiring at least about 1 ppm of carbon dioxide for stabilization, and the first selective dissolved gas is carbon dioxide.

9. The multi-chamber container of claim 2, wherein the volume of the headspace is from about 5% to about 100% of the volume of the solution in the multi-chamber container.

10. The multi-chamber container of claim 2, wherein the volume of the headspace is from about 35% to about 45% of the volume of the solution in the multi-chamber container.

11. The multi-chamber container of claim 2, wherein the multi-chamber container is terminally heat-sterilized.

12. The multi-chamber container of claim 2, wherein the at least one first compound is a selenium compound in a form of Se (IV).

13. The multi-chamber container of claim 12, wherein the at least one selenium compound is selected from the group consisting of sodium selenite, potassium selenite, lithium selenite, calcium selenite, magnesium selenite, selenous acid and selenium dioxide.

14. The multi-chamber container of claim 12, wherein the first solution has an acidic pH value in a range from about 1 to about 4.

15. The multi-chamber container of claim 2, wherein the headspace of the first selective dissolved gas stabilizes the at least one first compound for a time selected from the group consisting of at least 3 months, at least 6 months, at least 12 months, at least 18 months, and at least 24 months when stored at a temperature between about 1° C. and about 30° C.

16. The multi-chamber container of claim 15, wherein the multi-chamber container is stored at a temperature between about 18° C. and about 25° C.

17. The multi-chamber container of claim 2, wherein the multi-chamber container is selected from the group consisting of a four-chamber container, a five-chamber container, a six-chamber container, a seven-chamber container, and an eight-chamber container.

18. The multi-chamber container of claim 2, wherein the multi-chamber container further comprises:
(c) the second chamber containing a carbohydrate formulation;
(d) third chamber containing an amino acid formulation; and
(e) fourth chamber containing a lipid formulation.

19. The multi-chamber container of claim 18, wherein the multi-chamber container is made of a material having an oxygen barrier of less than 5cc/m$^2$/day.

20. The multi-chamber container of claim 2, wherein the at least one first chamber and the fourth chamber do not comprise any port tube.

21. The multi-chamber container of claim 2, wherein the at least one first compound requiring a first selective dissolved gas for stabilization comprises.

22. The multi-chamber container of claim 21, wherein the at least one micronutrient is at
least one selenium compound in the form of Se (IV), and the first selective dissolved gas is dissolved oxygen (DO).

23. The multi-chamber container of claim 22, wherein the at least one selenium compound is selected from the group consisting of sodium selenite, selenous acid and selenium dioxide.

24. The multi-chamber container of claim 22, wherein the concentration of the dissolved oxygen (DO) in the first solution at the time of sterilization is at least 6 ppm.

25. The multi-chamber container of claim 23, wherein the at least one selenium compound is sodium selenite or selenium dioxide.

26. The multi-chamber container of claim 21, wherein the multi-chamber container comprises at least five chambers.

27. The multi-chamber container of claim 21, wherein the first solution of the at least one first chamber comprises equal or above 0.5 ppm dissolved oxygen (DO) throughout shelf life of the medical product.

28. The multi-chamber container of claim 21, wherein the first solution of the at least one first chamber comprises from about 0.5 ppm to about 8 ppm dissolved oxygen (DO).

29. The multi-chamber container of claim 21 wherein the first solution of the at least one first chamber comprises equal or above 1 ppm dissolved oxygen (DO).

30. The multi-chamber container of claim 21, wherein the multi-chamber container is terminally heat-sterilized.

31. The multi-chamber container of claim 21, wherein the volume of the headspace is from about 5% to about 100% of the volume of the first solution in the multi-chamber container.

32. The multi-chamber container of claim 21, wherein the volume of the first headspace of the oxygen is from about 35% to 45% of the volume of the first solution in the multi-chamber container.

33. The multi-chamber container of claim 21, wherein the first first selective dissolved gas stabilizes the at least one micronutrient for a time selected from the group consisting of at least 3 months, at least 6 months, at least 12 months, at least 18 months, and at least 24 months when stored at a temperature between about 1° C. and about 30° C.

34. The multi-chamber container of claim 33, wherein the multi- chamber container is stored at a temperature between about 18° C. and about 25° C.

35. The multi-chamber container of claim 21, wherein the multi- chamber container is made of a material having an oxygen barrier less than 0.5 cc/m2/day.

36. The multi-chamber container of claim 21, wherein the multi- chamber container is made of a material having an oxygen barrier less than 2 cc/m2/day.

37. The multi-chamber container of claim 21, wherein the multi- chamber container is made of a material having an oxygen barrier less than 1 cc/m2/day.

38. The multi-chamber container of claim 21, wherein the first solution has an acidic pH value in a range from about 2.5 to about 3.2.

39. The multi-chamber container of claim 21, wherein the at least one second chamber contains a second solution selected from the group consisting of a carbohydrate formulation, an amino acid formulation, a lipid formulation, a vitamin formulation and a trace elements formulation.

* * * * *